(12) United States Patent
De Lucchi et al.

(10) Patent No.: US 9,932,361 B2
(45) Date of Patent: Apr. 3, 2018

(54) CONVENIENT PROCESS FOR THE PREPARATION OF STATINS

(71) Applicant: F.I.S.—FABBRICA ITALIANA SINTETICI S.P.A., Montecchio Maggiore (IT)

(72) Inventors: Ottorino De Lucchi, Venice (IT); Stefano Tartaggia, Venice (IT); Clark Ferrari, Brogliano (IT); Marco Galvagni, Verona (IT); Marta Pontini, Montebelluna (IT); Stefano Fogal, Brendola (IT); Riccardo Motterle, Arcugnano (IT); Rosa Maria Moreno, Barcelona (ES); Alex Comely, Barcelona (ES)

(*) Notice: Subject to any disclaimer, the term of this patent is extended or adjusted under 35 U.S.C. 154(b) by 0 days.

(21) Appl. No.: 15/063,966

(22) Filed: Mar. 8, 2016

(65) Prior Publication Data

US 2016/0200744 A1 Jul. 14, 2016

Related U.S. Application Data

(62) Division of application No. 14/395,703, filed as application No. PCT/EP2014/052627 on Feb. 11, 2014, now Pat. No. 9,315,470.

(30) Foreign Application Priority Data

Feb. 20, 2013 (IT) .............................. VI2013A0039
Sep. 18, 2013 (EP) ..................................... 13185030

(51) Int. Cl.

| | | |
|---|---|---|
| C07F 7/18 | (2006.01) | |
| C07D 239/42 | (2006.01) | |
| C07D 317/30 | (2006.01) | |
| C07D 215/14 | (2006.01) | |
| C07D 209/24 | (2006.01) | |
| C07D 413/12 | (2006.01) | |
| C07D 419/12 | (2006.01) | |
| B01J 27/13 | (2006.01) | |
| B01J 31/12 | (2006.01) | |
| C07D 209/12 | (2006.01) | |
| C07D 213/30 | (2006.01) | |

(52) U.S. Cl.
CPC ............. *C07F 7/1868* (2013.01); *B01J 27/13* (2013.01); *B01J 31/122* (2013.01); *C07D 209/12* (2013.01); *C07D 209/24* (2013.01); *C07D 213/30* (2013.01); *C07D 215/14* (2013.01); *C07D 239/42* (2013.01); *C07D 317/30* (2013.01); *C07D 413/12* (2013.01); *C07D 419/12* (2013.01); *C07F 7/188* (2013.01); *C07F 7/1844* (2013.01); *C07F 7/1892* (2013.01); *B01J 2231/543* (2013.01)

(58) Field of Classification Search
CPC ....................................................... C07F 7/11
See application file for complete search history.

(56) References Cited

U.S. PATENT DOCUMENTS

2011/0207172 A1  8/2011  Fogal et al.
2012/0310000 A1  12/2012  Lin et al.

FOREIGN PATENT DOCUMENTS

| EP | 0521471 A1 | 1/1993 |
|---|---|---|
| JP | 03048641 A | 3/2001 |
| WO | WO-03044011 A1 | 5/2003 |
| WO | WO-03064392 A1 | 8/2003 |
| WO | WO-2004096237 A2 | 11/2004 |
| WO | WO-2005056004 A1 | 6/2005 |
| WO | WO-2005063728 A2 | 7/2005 |
| WO | WO-2007017117 A1 | 2/2007 |
| WO | WO-2009118598 A1 | 10/2009 |
| WO | WO-2009128091 A2 | 10/2009 |
| WO | WO-2010077062 A2 | 7/2010 |
| WO | WO-2011000693 A1 | 1/2011 |
| WO | WO-2011124050 A1 | 10/2011 |

OTHER PUBLICATIONS

Bariotaki et al., Organic Letters (2012), 14(7), 1792-1795.*
Koboyashi et al. Total syntheses of macrosphelides C, F, G and H Letters in Organic Chemistry (2004), 1(4), 297-307.*
Koboyashi et al., Tetrahedron Letters (2002), 43(24), 4381-4384.*
Chen, K-M., et al., "1,3-Syn Diastereoseiective Reduction of β-Hydroxyketones Utilizing Alkoxydialkylboranes," Tetrahedron Letters 28(2)155-158, Pergamon. Press, England (1987).
Date, S.M.., et al., "A Rapid and Efficient Synthesis of a Bifunctional β-Silyiketone, Precursor for a Solid Supported β-Silylethanol Anchoring Group," Synthetic Communications 34(3):405-411, Marcel Dekker, Inc., United States (2004).
European Search Report and Search Opinion for EP Application No. EP13185030.7, Munich, Germany, dated Oct. 25, 2013, 7 pages.
Fan, W., et. al., "Acid-labile δ-ketal-β-hydroxy Esters by Asymmetric Hydrogenation of Corresponding δ-ketal-β-keto Esters in the Presence of $CaCO_3$," Chemical Communications 48(35):4247-4249, Royal Society of Chemistry, England (2012).
International Search Report for International Application No. PCT/EP2014/052627, European Patent Office, The Netherlands, dated Aug. 1, 2014, 7 pages.
Yamada, T., et al., "Absolute Stereostructures of Cell Adhesion Inhibitors, Macrosphelides H and L, from *Periconia byssoides* OUPS-N133," The Journal of Antibiotics 55(2):147-154, Japan Antibiotics Research Association, Japan (2002).

* cited by examiner

*Primary Examiner* — Paul V Ward
(74) *Attorney, Agent, or Firm* — Sterne, Kessler, Goldstein Fox

(57) ABSTRACT

Object of the present invention is an improved process for the preparation of key intermediates for the synthesis of statins.

4 Claims, No Drawings

CONVENIENT PROCESS FOR THE PREPARATION OF STATINS

This Application is a divisional of U.S. application Ser. No. 14/395,703, filed Oct. 20, 2014, which claims priority to the International Application No. PCT/EP2014/052627, filed Feb. 11, 2014, which claims the benefits of Italian Application No. VI2013A000039, filed Feb. 20, 2013, and European Application No. 13185030.7, filed Sep. 18, 2013, each of which is incorporated by reference in its entirety.

TECHNICAL FIELD

The present invention refers to an improved process for the preparation of key intermediates for the synthesis of Statins which is a class of active pharmaceutical ingredients.

BACKGROUND ART

Statins are a class of pharmaceutical active ingredients inhibitors of the 3-Hydroxy-3-Methylglutaryl-Coenzime A (HMG-CoA) reductase, the enzyme that catalyzes the conversion of HMG-CoA to Mevalonate, a limiting agent of the biosynthesis of Cholesterol and they are therefore used against all the forms of hypercholesterolemia, for the regression of the atherosclerotic plaque and for the prevention of cardiovascular events.

The first statin to be discovered and commercialized was Mevastatin, having the following structure:

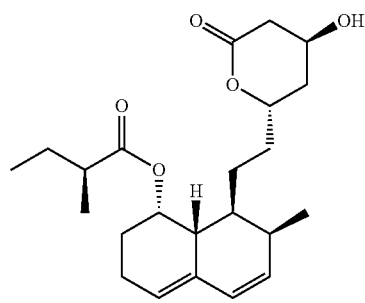 [SMILES: CC[C@H](C)C(=O)O[C@H]1CCC=C2C=C[C@H](C)[C@H](CC[C@H]3C[C@H](O)CC(=O)O3)[C@H]21]

After that, other natural statins have been discovered and commercialized as Pravastatin having the following chemical structure:

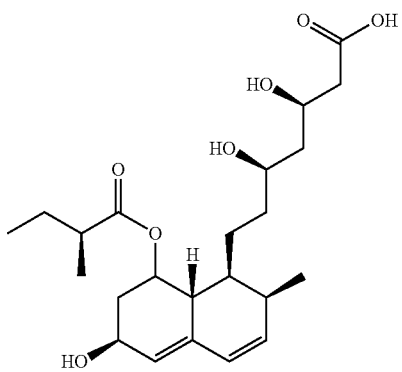 [SMILES: CC[C@H](C)C(=O)OC1C[C@H](O)C=C2C=C[C@H](C)[C@H](CC[C@@H](O)C[C@@H](O)CC(=O)O)[C@H]21]

or such as Lovastatin (in acid form) having the following chemical structure:

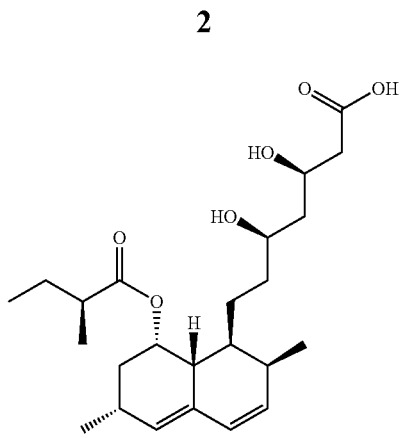

All the above statins are characterised in that they comprise a similar dicyclohexyl skeleton bounded with the same seven member alkyl chain, having two hydroxyl groups bounded to two asymmetric carbon atoms. Such chain can be in cyclic "lactone form" or in open "acid form".

Thus, Lovastatin, is typically present in "lactone form", being described with the following chemical formula:

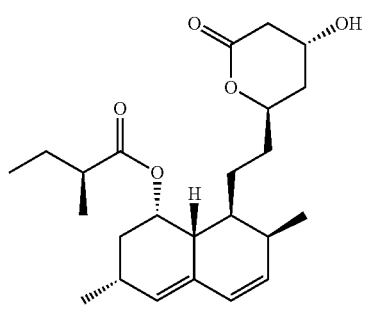 [SMILES: CC[C@H](C)C(=O)O[C@H]1C[C@@H](C)C=C2C=C[C@H](C)[C@H](CC[C@@H]3C[C@@H](O)CC(=O)O3)[C@H]21]

wherein both side chain hydroxyls have R configuration.

Another important statin of this type is Simvastatin, typically present in the lactone form, identified with the following structure:

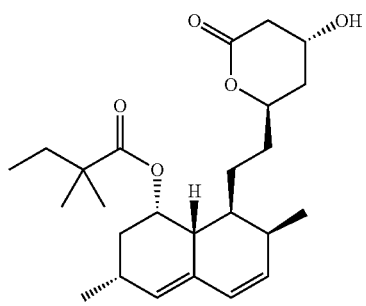 [SMILES: CCC(C)(C)C(=O)O[C@H]1C[C@@H](C)C=C2C=C[C@H](C)[C@H](CC[C@@H]3C[C@@H](O)CC(=O)O3)[C@H]21]

Simvastatin in acid form has the following chemical structure:

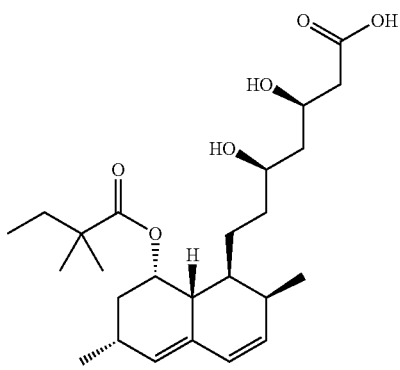 [SMILES: CCC(C)(C)C(=O)O[C@H]1C[C@@H](C)C=C2C=C[C@H](C)[C@H](CC[C@@H](O)C[C@@H](O)CC(=O)O)[C@H]21]

wherein both side chain hydroxyls have R configuration.

In the more recent years a new type of statins have been discovered and marketed such as Fluvastatin, Cerivastatin, Rosuvastatin and Pitavastatin.

Rosuvastatin has the following structure formula:

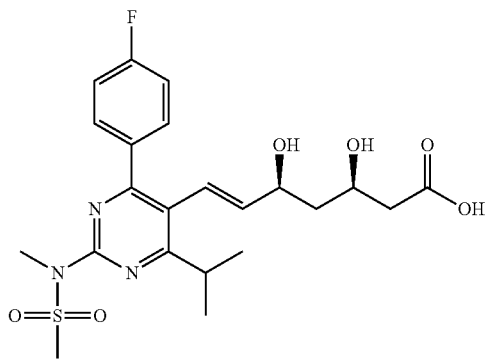 [SMILES: CC(C)c1nc(N(C)S(C)(=O)=O)nc(-c2ccc(F)cc2)c1/C=C/[C@@H](O)C[C@@H](O)CC(=O)O]

and has chemical name (E)-(3R,5S)-7-[4-(4-Fluorophenyl)-6-isopropyl-2-[(methylsulfonyl) (methyl) amino]pyrimidin-5-yl]-3,5-dihydroxyhept-6-enoic acid. Rosuvastatin is currently marketed as calcium salt (Rosuvastatin calcium), or better as hemicalcium salt and with commercial name of Crestor.

Cerivastatin has the following formula:

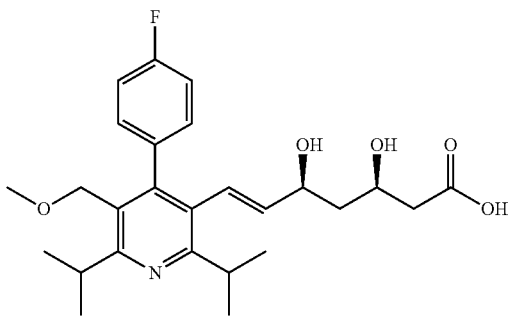 [SMILES: COCc1c(C(C)C)nc(C(C)C)c(/C=C/[C@@H](O)C[C@@H](O)CC(=O)O)c1-c1ccc(F)cc1]

Pitavastatin has the following formula:

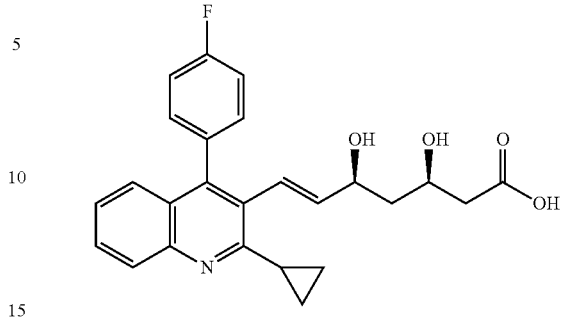

Fluvastatin has the following formula:

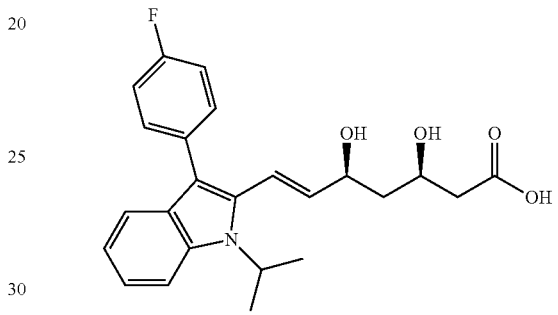

The second type of statins are characterized by a double bond with trans (E) geometry in the side chain.

Many classic synthetic approaches for the synthesis of statins, particularly for those having E geometric isomerism, have been developed during the last decades. Many methods comprise an olefination reaction (Wittig, Horner-Emmons or Julia reactions) carried out between the side chain functionalized by means of phosphorous, phosphorane or sulphone groups with suitable aldehydes comprising the core structure of statins. However all these methods have the drawback that the reaction is not always very selective towards the trans (E) isomer, thus also forming the cis (Z) isomer which is an impurity that is often difficult to remove. Another big drawback is that the side products of the reaction are phosphin oxides or sulphur compounds. These substances are difficult to remove from the reaction mixtures, thus increasing the whole cost of the synthesis of statins. Moreover, the molar weight of phosphorous, phosphorane or sulphone reagents, e.g. triphenylphosfine ylides, is very high when compared with the molecular weight of the side chain and thus the productivity of the process is quite low since it is necessary to handle large amounts of reagents to obtain a relatively low amounts, in terms of kilograms, of products.

An example of this known reaction, directed to the preparation of Rosuvastatin, is described in EP0521471A1, or more recently in WO2009/128091 and WO2009/118598.

SUMMARY OF INVENTION

The problem addressed by the present invention is therefore that of providing an improved process for the preparation of statins and salts thereof which allows to get round to the drawbacks above reported with reference to the known prior art.

This problem is solved by a process for the preparation of a key intermediate for the synthesis of statins and salts thereof as outlined in the annexed claims, whose definitions are integral part of the present description.

Further features and advantages of the process according to the invention will result from the description hereafter reported of examples of realization of the invention, provided as an indication and not as a limitation of the invention.

DESCRIPTION OF EMBODIMENTS

Object of the present invention is a process for the preparation of the compound of formula (I):

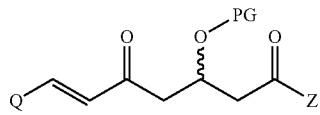
(I)

which is a key intermediate for the synthesis of statins and salts thereof, wherein Z is selected from the group comprising OH, O⁻, OR, SR, O(CO)OR, $NH_2$, NHR, $NR_2$ wherein R is selected between linear or branched $C_{1-7}$ alkyl, linear or branched $C_{1-7}$ alkenyl or alkynyl, $C_{3-7}$ cycloalkyl, aryl-$C_{0-4}$ alkyl and wherein in $NR_2$ the two R groups can also be joined forming a $C_{2-10}$ alkyl or alkenyl ring; PG is a hydroxyl protecting group selected in the group comprising THP, camphanoyl, bornyl, menthyl, R, (CO)R, $CH_2OR$, $CH_2SR$, $SiR_3$ wherein the substituent R can be equal or different in $SiR_3$ and R is selected between linear or branched $C_{1-7}$ alkyl, linear or branched $C_{1-7}$ alkenyl or alkynyl, $C_{3-7}$ cycloalkyl, aryl-$C_{0-4}$ alkyl; and Q is selected in the group comprising the following radicals:

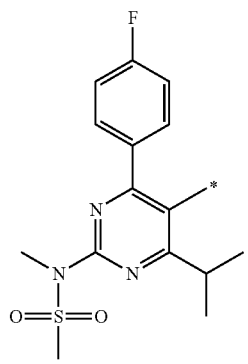
(a)

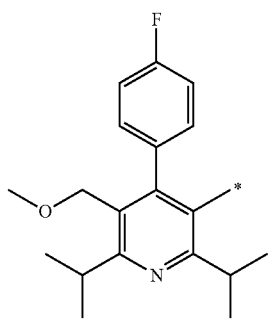
(b)

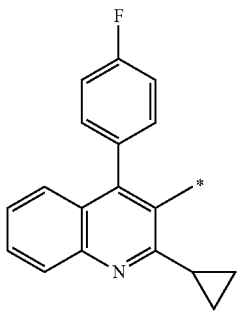
(c)

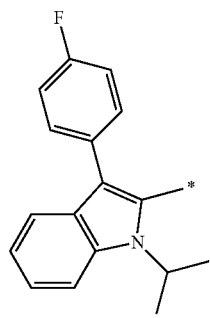
(d)

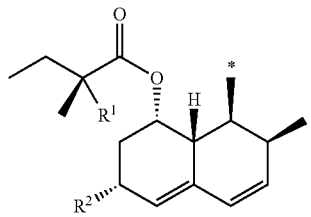
(e)

wherein the symbol * specifies the bonding position; and $R^1$ is hydrogen or methyl; and $R^2$ is chosen between hydrogen, methyl, hydroxyl, hydroxymethyl and O—PG wherein PG has the same meaning as defined above; comprising the reaction of the compound of formula (II):

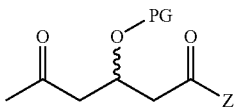
(II)

wherein PG and Z are the same as in the compound of formula (I), with the compound of formula (III):

(III)

wherein Q is the same as in the compound of formula (I).

It has been indeed surprisingly found that the key intermediate for the synthesis of statins and salts thereof of formula (I) can be prepared, using the intermediate of formula (II) which does not contain any phosphorus or sulfur atom, thus avoiding the problems related to the waste disposal. Moreover, the resulting product of formula (I) does not contain the (Z) isomer impurity since this reaction is highly regioselective.

Hence, the compound of formula (I) according to the present invention has the double bond in trans (E) configuration, since this reaction provides selectively only trans (E) product.

The R substituent, part of the Z group or of PG group, is selected between linear or branched $C_{1-7}$ alkyl, linear or branched $C_{1-7}$ alkenyl or alkynyl, $C_{3-7}$ cycloalkyl, aryl-$C_{0-4}$ alkyl;

The linear or branched $C_{1-7}$ alkyl group can also be, unsubstituted or substituted with one, two or three substituents chosen in the group of hydroxyl and $C_1$-$C_5$ alkoxy.

The definition of linear or branched $C_{1-7}$ alkyl thus includes methyl, ethyl, n-propyl, isopropyl, n-butyl, isobutyl, sec-butyl, tert-butyl, n-pentyl, neopentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 3-ethylbutyl, 1,1-diethylethyl, 1-propylpropyl, n-heptyl, etc.

According to a preferred embodiment, Z is OR, i.e. the gamma keto esters are the preferred compounds of formula (I) and (II).

According to a more preferred embodiment, Z is OR wherein R is $C_{1-4}$ alkyl group, being at most preferred the following groups: OMe, OEt, Ot-Bu.

R can also be $C_{3-7}$ cycloalkyl, for example, cyclohexyl.

R can also be an aryl-$C_{0-4}$ alkyl wherein an aryl group is for example a $C_6$-$C_{12}$ aryl group, preferably phenyl, naphthyl, 4-nitrophenyl. The groups benzyl, phenylethyl and 4-nitrobenzyl are preferred.

For the compounds of formula (I) and (II), every Z group which is able to remain unreacted during the reaction of the present invention but that can be removed in later steps to provide statins, should be intended as included in the scope of protection of the present invention.

PG is a hydroxyl protecting group selected in the group comprising THP, camphanoyl, bornyl, menthyl, R, (CO)R, $CH_2OR$, $CH_2SR$, $SiR_3$ wherein the substituent R can be equal or different in $SIR_3$ and R is selected between linear or branched $C_{1-7}$ alkyl, linear or branched $C_{1-7}$ alkenyl or alkynyl, $C_{3-7}$ cycloalkyl, aryl-$C_{0-4}$ alkyl.

PG can also be a tryalkylsilyl group having formula $SiR_3$ wherein this group includes trimethylsilyl (TMS), t-Butyldimethylsilyl (TBDMS or TBS), being preferred TBDMS.

PG can also be a group (CO)R wherein R is a linear or branched $C_{1-7}$ alkyl which means that the hydroxyl group is protected by an ester group, preferably can be the acetate group.

PG can also be a group (CO)R wherein R is a aryl-$C_{0-4}$ alkyl, thus it can be preferably an aromatic ester, such as phenyl, 4-nitrophenyl, benzyl or 4-nitrobenzyl.

PG can also be an acetal having the structure $OCH_2OR$ or $OCH_2SR$.

PG can also be R, preferably, t-butyl, alkenyl such as allyl, benzyl, p-methoxybenzyl, phenyl, p-methoxyphenyl.

At last, PG can also be tetrahydropyranyl (THP) or racemic camphanoyl, (R)-camphanoyl or (S)-camphanoyl, racemic bornyl, (+) or (−) bornyl, racemic menthyl, (+) or (−) menthyl.

The compounds of formula (I) and (II) comprise either the R enantiomer, or the S enantiomer, or the racemic mixture or their mixtures in any R/S ratio.

In a preferred embodiment, the process of the present invention provides the compound of formula (I) which has the following formula (I-R):

wherein the hydroxyl protected group in the side chain has R configuration.

The process for the preparation of the compound of formula (I) in which the protected hydroxyl group has R configuration is preferred, since this is the stereochemistry requested for the preparation of the marketed statins.

Thus, the process is preferred wherein the product of formula (I) has the following formula (I-R):

wherein the protected hydroxyl group in the side chain has R configuration.

Preferably the process of the present invention is intended for the preparation of Rosuvastatin, Pitavastatin or Fluvastatin.

Thus, the most preferred process is that wherein Q is the following radical:

(a)

The process according to the invention can be carried out in the presence of one or more solvents such as toluene, xilene, halogenated solvents, $CH_2Cl_2$, DMF, NMP, DMSO, THF, Dioxane, MTBE, diethyl ether and alcohols. Preferably the reaction is carried out in an ether solvent such as Methyl-t-Butyl ether (MTBE), Dioxane, Methyl-THF, tetrahydrofuran (THF), being more preferred THF.

The process of this invention can be carried out at a temperature comprised in the range from about −50° C. to about 100° C., preferably from about 0° C. to 20° C., more preferably about 0° C.

According to a preferred embodiment, the process of the present invention is carried out using from 1.05 to 2.0 molar equivalents of the compound of formula (II) in respect to the compound of formula (III), more preferably about 1.2 molar equivalents since it provides higher molar yields of the compound of formula (I).

The trials to perform the process of the present invention under the typical aldol condensation conditions, i.e. under mere basic conditions, failed. To this aim bases such as LiOH, NaOH, KOH, $K_2CO_3$ and amines, solvents such as MeOH, MeCN, THF, Toluene and performing the reaction at room temperature or at reflux have been tried. All the combinations of these conditions did not provide the compound of formula (I) by reaction of the compound of formula (II) with the compound of formula (III). In particular it was observed that using stoichiometric amount of base, the compound of formula (II) is subjected to decomposition and using catalytic amounts of base the reaction does not proceed. See Example 8.

It has been observed that the process of the present invention have to be carried out in presence of a Lewis acid.

The process according to the invention can be carried out in the presence of a catalyst, preferably the process is carried out in presence of a Lewis acid. The Lewis acid can be for example $TiCl_4$, $AlCl_3$, $ZrCl_4$, $ZnCl_2$, $FeCl_3$, $BF_3$, $BBr_3$, $SnCl_4$, $SbCl_5$, etc.

According to a more preferred embodiment, the process of this invention can be carried out in presence of $TiCl_4$ or $AlCl_3$, and more preferably in presence of $TiCl_4$ because it provides the higher molar yields.

The amounts of Lewis acid employed in comparison with the sum of the moles of the compounds of formula (III) and (II) are comprised between 0.5 and 4.0 molar equivalents.

The preferred amount of Lewis acid is comprised between 2.0 and 3.0 molar equivalents, being more preferred 2.2 molar equivalents because these amounts provides the higher molar yields.

According to a preferred embodiment, the process of the present invention is carried out in presence of a Lewis acid together with a base since that the reaction between the compounds of formula (II) and (III) to provide the compound of formula (I) provides the better results in presence of a Lewis acid and a base. Thus, according to a more preferred embodiment, the process of the present invention is carried out in presence of a Lewis acid and a base.

The process according to the invention can be carried out in the presence of a base such as an organic amine of general formula $NR_3$ with R being linear or branched $C_{1-7}$ alkyl and the three R groups can be the same or different. The amine can also be selected among pyrrolidine, N-alkyl substituted pirrolydine, piperidine, morpholine, N-alkyl substituted piperidine and N-alkyl substituted morpholine. Suitable bases are for instance N-Methylmorpholine, Triethylamine, DABCO, Ethyldiisopropriamine and TMEDA (Tetramethylethylendiamine), DIPEA (diisopropylethylamine), phosphoramidates. The N-methylmorpholine is preferred since it provides higher molar yields.

Also other bases can be used to carry out the process of the present invention such as acetates, bicarbonates, carbonates, hydroxides, phosphates, alcoholates of alkaline or alkaline-heart metals.

According to a preferred embodiment of the present invention, the process of the present invention is carried out in presence of a Lewis acid and an organic base.

The amounts of base employed to carry out the process of the present invention are comprised between 1 and 8 molar equivalents in respect to the sum of the moles of the compounds of formula (III) and (II).

The preferred amount of base are comprised between 4.0 and 6.0 molar equivalents, being more preferred 4.4 because they provide the higher molar yields.

In general the best amount of the base is the double of the amount of Lewis acid used. Thus, for instance, when 2.2 molar equivalents of Lewis acid are used, 4.4 molar equivalents of base should be conveniently used.

According to a preferred embodiment of the invention, the process is carried out in presence of between 0.5 and 4.0 molar equivalents of Lewis acid and between 1 and 8 molar equivalents of base, both in respect to the sum of the moles of the compounds of formula (III) and (II).

According to a more preferred embodiment of the invention, the process is carried out in presence of between 2.0 and 3.0 molar equivalents of Lewis acid and between 4.0 and 6.0 molar equivalents of base, both in respect to the sum of the moles of the compounds of formula (III) and (II).

According to the best embodiment of the invention, the process is carried out in presence of 2.2 molar equivalents of Lewis acid and 4.4 molar equivalents of base, both in respect to the sum of the moles of the compounds of formula (III) and (II).

According to a preferred embodiment of the invention, the process of this invention can be carried out in the presence of $TiCl_4$ and N-methylmorpholine since this combination provides the best results in terms of molar yields.

According to a preferred embodiment of the invention, the process is carried out in presence of between 0.5 and 4.0 molar equivalents of $TiCl_4$ and between 1 and 8 molar equivalents of N-methylmorpholine, both in respect to the sum of the moles of the compounds of formula (III) and (II).

According to a more preferred embodiment of the invention, the process is carried out in presence of between 2.0 and 3.0 molar equivalents of $TiCl_4$ and between 4.0 and 6.0 molar equivalents of N-methylmorpholine, both in respect to the sum of the moles of the compounds of formula (III) and (II).

According to a more preferred embodiment, the process of the present invention is performed in presence of 2.2 molar equivalents of $TiCl_4$ and 4.4 molar equivalents of N-methylmorpholine, both in respect to the sum of the moles of the compounds of formula (III) and (II), because it provides the best results in terms of molar yield of the compound of formula (I). Indeed, using 2.2 mol. equivalents of $TiCl_4$ and 4.4 molar equivalents of N-methylmorpholine, conversions around 85% are achieved.

Changing order of addition of the reagents does not effect the molar yield of the process since that adding (dropwise) a mixture of the compound of formula (III) and Lewis acid to a mixture of the compound of formula (II) and base does not afford an higher conversion and/or isolated molar yield of the product of formula (I).

Contrarily to the typical condition used in the aldol condensation where the reaction is performed at basic pH values, the pH measured in the process according to the present invention is, at the begin of the reaction, about 7.0-7.5 and about 4.0-5.0 at the end of the reaction. Furthermore, the aldol compound, typical intermediate of the aldol condensation, has never been observed in the process of the present invention.

The Table I of example 9 shows the effect of the various Lewis acid, bases and molecular equivalents thereof on the molar yield of the process of the present invention.

The molar yield of the process of the invention is comprised between 70% and 80%.

The process parameters, including the kind of Lewis acid, of base, equivalents thereof, solvents, volumes, temperatures, etc. as explained in the previous pages, can be combined in any combination to perform the process of the present invention. Examples of such combinations are provided in the experimental section.

It should be noticed that performing the process of the present invention using a compound of formula (II) wherein the hydroxyl function is not protected by an hydroxyl protecting group PG as that of the present invention, only poor results are achieved in terms of molar yield of the product since many side reactions occur. To increase the molar yield it would be necessary to employ al least 3 molar equivalents of the ketoalcohol reactant that is not economically convenient and, however, the reaction does not work well. Example 10 shows the experimental trials aimed to explore the reaction of the compound (II) without hydroxyl protection with the compound of formula (III). Only poor yields were achieved.

Thus, in order to prepare the compound of formula (I) having the hydroxyl unprotected, it is much better to perform the process according to the present invention and then remove the protecting group PG rather than to perform the direct coupling of the compound (II) having the hydroxyl unprotected with the compound of formula (III). The protecting group PG in the compound of formula (II) plays thus an important role in the process of the present invention.

The process of the present invention thus also provides the compound of formula (I-e):

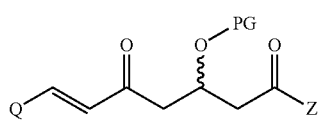

wherein Z is selected from the group comprising OH, O⁻, OR, SR, O(CO)OR, $NH_2$, NHR, $NR_2$ wherein R is selected between linear or branched $C_{1-7}$ alkyl, linear or branched $C_{1-7}$ alkenyl or alkynyl, $C_{3-7}$ cycloalkyl, aryl-$C_{0-4}$ alkyl and wherein in $NR_2$ the two R groups can also be joined forming a $C_{2-10}$ alkyl or alkenyl ring; PG is a hydroxyl protecting group selected in the group comprising THP, camphanoyl, bornyl, menthyl, R, (CO)R, $CH_2OR$, $CH_2SR$, $SiR_3$ wherein the substituent R can be equal or different in $SiR_3$ and R is selected between linear or branched $C_{1-7}$ alkyl, linear or branched $C_{1-7}$ alkenyl or alkynyl, $C_{3-7}$ cycloalkyl, aryl-$C_{0-4}$ alkyl; and Q is the following radical:

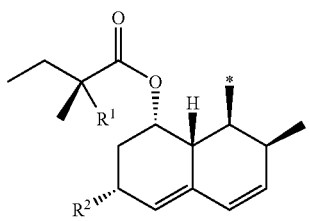

wherein $R^1$ is hydrogen or methyl; and $R^2$ is chosen between hydrogen, methyl, hydroxy, hydroxymethyl and O—PG wherein PG has the same meaning as defined in this paragraph; with the exception of the compound wherein $R^1$ and $R^2$ are hydrogen, PG is TBDMS, Z is OMe and the configuration of the protected hydroxyl group in the side chain is R or S.

The conversion of the compound of formula (I) to statins in which the double bond is not present such as, e.g. Lovastain, can be performed with a reactant able to provide hydride ions, such as, e.g. sodium borohydride. These reagents allow the selective reduction of the double bond in the side chain without reducing the diene function.

After the double bond reduction, as for all the other statins, the hydroxyl protecting group can be cleaved and then the carbonyl group in the side chain can be diasteroselectively reduced to produce the second chiral center in the side chain.

Alternatively, the conversion of the compound of formula (I) to statins in which the double bond is not present such as, e.g. Lovastain, can be performed first cleaving the hydroxyl protecting group, and then reducing the double bond, thus preparing the compound of formula (I-e-bis) from the compound of formula (I-e).

The process of the present invention therefore provides also the compound of formula (I-e-bis):

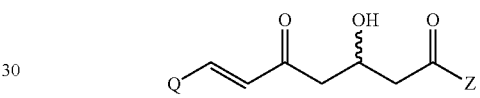

wherein Z is selected from the group comprising OH, O⁻, OR, SR, O(CO)OR, $NH_2$, NHR, $NR_2$ wherein R is selected between linear or branched $C_{1-7}$ alkyl, linear or branched $C_{1-7}$ alkenyl or alkynyl, $C_{3-7}$ cycloalkyl, aryl-$C_{0-4}$ alkyl and wherein in $NR_2$ the two R groups can also be joined forming a $C_{2-10}$ alkyl or alkenyl ring; and Q is the following radical:

(e)

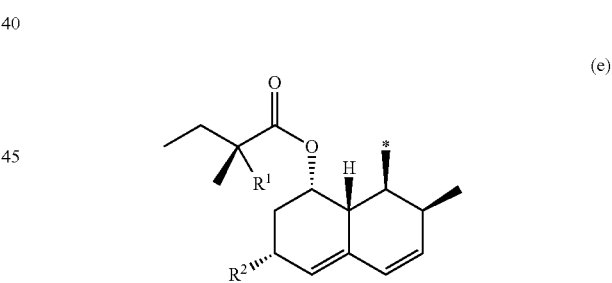

wherein $R^1$ is hydrogen or methyl; and $R^2$ is chosen between hydrogen, methyl, hydroxy, hydroxymethyl and O—PG wherein PG has the same meaning as defined above; with the exception of the compounds wherein $R^1$ and $R^2$ are hydrogen, Z is OH, OMe or O-(1-(R)-phenylethyl) and the configuration of the hydroxyl group in the side chain is R.

The compounds of formula (I-e) or of formula (I-e-bis) selected in the group comprising: $R^1$ and $R^2$ are methyl, $R^1$ is hydrogen and $R^2$ is methyl, $R^1$ and $R^2$ are hydrogen, $R^1$ is hydrogen and $R^2$ is hydroxyl; are preferred since they are those involved in the preparation of marketed statins.

The process of the present invention also provides compound of formula (I-b; Z=OtBu):

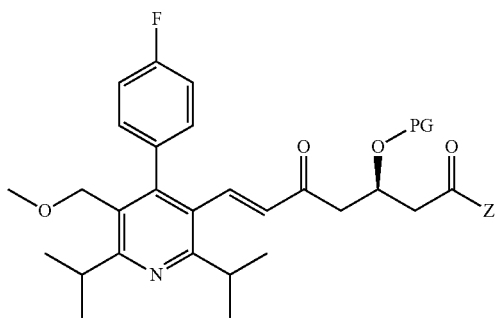

or compound of formula (I-d; Z=Ot-Bu):

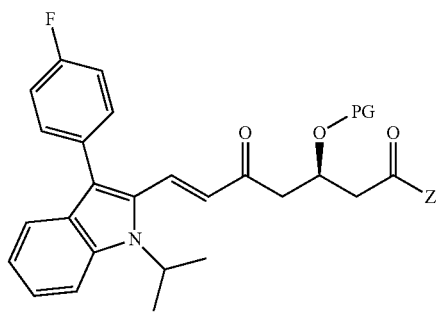

wherein the protected hydroxyl group in the side chain has R configuration, and Z, is OtBu and PG is a hydroxyl protecting group as defined above.

The present invention also provides and employs the compound of formula (II):

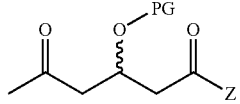

wherein PG and Z are the same as in the compound of formula (I), with the exceptions of the following compounds:

Z is OEt, PG is TBDMS, in racemic form or having R configuration;

Z is OMe, PG is 4-Bromobenzoyl, having R configuration;

Z is NH(t-Bu) or O(t-Bu), PG is 4-Nitrobenzoyl, in racemic form;

Z is O(t-Bu), PG is (S) or (R) alpha-methoxy Phenylacetyl, having S configuration;

Z is OMe, PG is (S)-camphanoyl (i.e. 2-oxobicyclo[2.2.1]heptanes-1-carboxylic acid, 4,7,7-trimethyl-3-oxo-(1S,4R)), having R or S configuration.

The configurations above described always refers to the configuration of the carbon bonded to the hydroxyl group.

The groups 4-Bromobenzoyl and 4-Nitrobenzoly have the following structures:

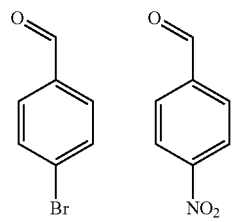 [SMILES: O=Cc1ccc(Br)cc1 ; O=Cc1ccc([N+](=O)[O-])cc1]

while the groups (S) or (R) alpha-methoxy Phenylacetyl have the following structure:

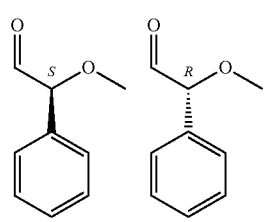

Finally, the group (S)-camphanoyl (i.e. 2-oxobicyclo[2.2.1]heptanes-1-carboxylic acid, 4,7,7-trimethyl-3-oxo-(1S,4R)) has the following structure:

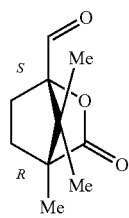

According to a preferred embodiment, the Z group in the compound (II) is O(t-Bu), with the exception of the compounds where:

PG is 4-Nitrobenzoyl, and is in racemic form, and
PG is (S) or (R) alpha-methoxy Phenylacetyl, having S configuration.

According to a more preferred embodiment, the preferred compound has the following formula (II-R; Z=OtBu):

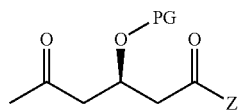

wherein the protected hydroxyl group in the side chain has R configuration, and Z is OtBu, and PG is a hydroxyl protecting group as defined above.

According a preferred embodiment, is also preferred the compound of formula (II) wherein PG is TBDMS, with the exception of the compounds where Z is OEt, in racemic form or having R configuration.

It is particularly preferred the compound of formula (II) wherein PG is TBDMS and Z is OMe.

The most preferred compound of formula (II) is that wherein PG is TBDMS, Z is OMe and has R configuration (see examples). This compound has the following structure:

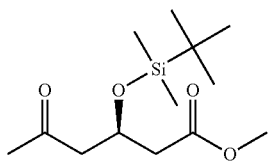 [SMILES: COC(=O)C[C@@H](CC(C)=O)O[Si](C)(C)C(C)(C)C]

The above compound is the most preferred since it is the best starting point for the cheaper synthesis of statins exploiting the process of the present inventions.

The compound of formula (II) having R configuration is a preferred general compound since the statins have that configuration on the carbon atom bonded to the hydroxyl group.

At least, it is important to underline that the compound of formula (II) is the key intermediate for the process of the present invention.

All the above compounds, prepared and employed by the process of the present invention, are useful intermediates for the preparations of statins or salts thereof comprised in the group of Rosuvastatin, Cerivastatin, Pitavastatin, Fluvastatin, Simvastatin, Lovastatin, Mevastatin, Pravastatin. Suitable salts are all the pharmaceutically acceptable salts.

In particular the compounds of formula (II) as described in the previous two pages, prepared and employed by the process of the present invention, are useful intermediates for the preparations of statins or salts thereof comprised in the group of Rosuvastatin, Cerivastatin, Pitavastatin, Fluvastatin, Simvastatin, Lovastatin, Mevastatin, Pravastatin. Suitable salts are all the pharmaceutically acceptable salts.

The compound of formula (I), or a salt thereof, can be converted to a statin or a salts thereof, according to known procedures, such as that described in WO 03064392 that typically include: a. cleavage of the hydroxyl protecting group, b. enantioselective reduction of the alpha-beta unsatured carbonyl, c. conversion (e.g. by hydrolysis) of the Z group to carboxyl group or to correspondent lactone form.

The compound of formula (II), can be prepared according to the following reaction scheme:

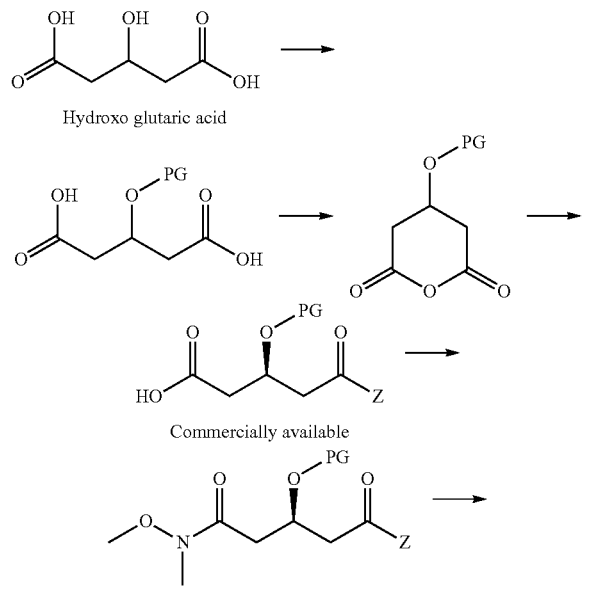

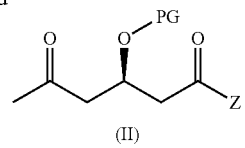

The above commercially available compound can be prepared for example by chemical desymmetrization of protected hydroxyglutaric anhydride as described in literature. This compound can react with 1,1'-carbonyldiimidazole to form the correspondent carbonyldiimidazole derivative which is then reacted with N,O-dimethylhydroxylamine to provide the correspondent Weinreb amide. The obtained intermediate is reacted with a Grignard reagent to provide the compound of formula (II).

The preparation of the compound of formula (II) can be performed applying the teachings of Chem. Comm., 2012, 48, 4247-4249; Japanese patent application JP 03048641 published on 1 Mar. 1991; or the Journal of antibiotics, 2002, Vol. 55, 147-154.; or described in Synth. Communication, 2004, 34, 405.

The compound of formula (III) is typically commercially available or can be prepared according to known procedures. Below are reported the commercial sources for such intermediate compounds of formula (III).

The following compounds can thus be considered as starting materials for the process of the present invention:

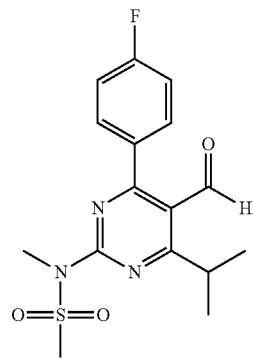 [SMILES: CC(C)c1nc(N(C)S(C)(=O)=O)nc(-c2ccc(F)cc2)c1C=O]

having chemical name N-[4-(4-fluorophenyl)-5-formyl-6-(propan-2-yl) pyrimidin-2-yl]-N-methylmethanesulfonamide which can be purchased from Toronto Research Chemicals Inc. or Ontario Chemicals, Inc. or prepared according to the teaching of EP521471;

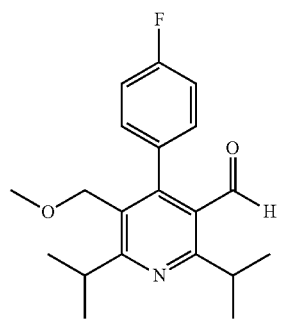 [SMILES: COCc1c(C(C)C)nc(C(C)C)c(C=O)c1-c1ccc(F)cc1]

having chemical name 4-(4-fluorophenyl)-5-(methoxymethyl)-2,6-di(propan-2-yl)pyridine-3-carbaldehyde can be purchased from American Custom Chemicals Corp;

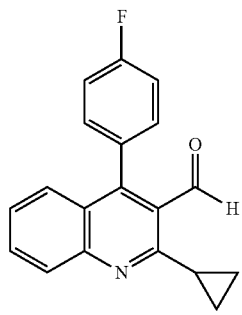 [SMILES: O=Cc1c(C2CC2)nc2ccccc2c1-c1ccc(F)cc1]

having chemical name 2-cyclopropyl-4-(4-fluorophenyl)quinoline-3-carbaldehyde can be purchased from Ontario Chemicals, Inc. or Novochemy Limited;

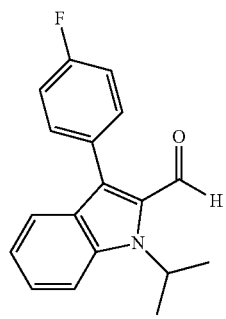 [SMILES: CC(C)n1c(C=O)c(-c2ccc(F)cc2)c2ccccc21]

having chemical name 3-(4-fluorophenyl)-1-(propan-2-yl)-1H-indole-2-carbaldehyde can be purchased from ABCR GmbH KG, or Novochemy Limited;

and the compound having the following chemical formula:

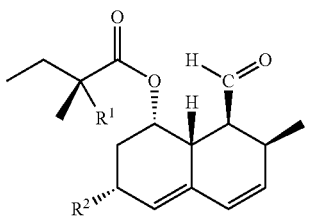

in which $R^1$ is hydrogen and $R^2$ is OTBS, wherein TBS is t-butyldimethylsilyl, or the compound in which $R^1$ and $R^2$ are methyl can be prepared according to the preparations disclosed on WO2004096237.

To prepare statins having the double bond in the side chain such as Rosuvastatin, Fluvastatin, etc. the hydroxyl protecting group can be cleaved and then the carbonyl group in the side chain can be diasteroselectively reduced to produce the second chiral center in the side chain; at last the Z function can be easily converted in the carboxylic or lactone function.

The side product of the process of the present invention is water therefore a substance much more easier to manage in comparison with the triphenylphosphine oxide or other compounds containing phosphorous or sulfur which are the side product of the nowadays known industrial processes, typically and largely employed for the preparation of these key intermediates.

Thus, the process of the present invention allows the production of key intermediates for the synthesis of statins in a much more economical way.

According to one improvement of the process of the present invention, the reaction between the compounds of formula (II) and (III) to provide the compound of formula (I) is carried out by means of Tin Tetrachloride ($SnCl_4$) as Lewis acid. This Lewis acid provide better results in comparison with the other Lewis acids, and also better results in comparison with $TiCl_4$ which was already selected as a preferable Lewis acid because of its better performances in terms of molar yield of the final product.

When Tin tetrachloride is used in the process according the present invention, the conversion of the compound of formula (III) into the compound of formula (I) is about 90-95%.

To perform the process of the present invention $SnCl_4$ can be used in amounts ranging from 2 to 3.5 molecular equivalents in respect of the compound of formula (III).

According to a preferred embodiment of the invention the process for the preparation of (I) is carried out in presence of Tin tetrahydrochloride and a base.

According to a more preferred embodiment of the invention the process for the preparation of (I) is carried out in presence of Tin tetrahydrochloride and N-Methylmorpholine.

The amount of N-Methylmorpholine used to perform the coupling of compounds of formula (II) and (III) to provide the compound of formula (I) is comprised between 2 and 6 molecular equivalents in respect of the compound of formula (III). Preferably, about 3 molecular equivalents of N-Methylmorpholine.

It is preferable to add the solution of N-Methylmorpholine to the other reactants in a time comprised between 1 and 2 hours, more preferably in about 1.5 hours because this addition rate allows to increase the molar yields of the final product.

All the combinations of the above process features can be employed to carry out the process of the present invention.

A large study has been carried out to find an suitable economical process for the preparation of the key intermediate, i.e. the compound having R configuration of formula (II-R):

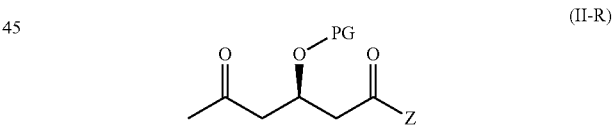

wherein PG and Z are the same as in the compound of formula (I) as defined above, since the compound of formula (II) having R configuration allows the preparation of the Statins pharmacologically actives.

These experiments allowed to set up a process for the preparation of the compound of formula (II-R):

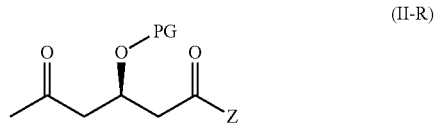

wherein PG and Z are the same as in the compound of formula (I) as defined above comprising the following steps:

(a) reducing the compound of formula (VII):

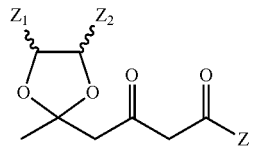

wherein $Z_1$ and $Z_2$ are equal or different and are chosen between hydrogen, R and (CO)OR, in which R is selected between linear or branched $C_{1-7}$ alkyl, linear or branched $C_{1-7}$ alkenyl or alkynyl, $C_{3-7}$ cycloalkyl, aryl-$C_{0-4}$ alkyl,
to obtain the compound of formula (VI):

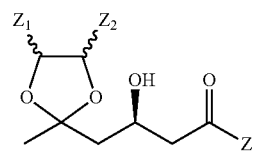

wherein Z, $Z_1$ and $Z_2$ have the same meanings as in the compound of formula (VII);
(b) protection of the hydroxyl group of the compound of formula (VI) to obtain the compound of formula (V):

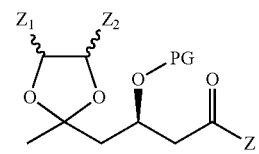

wherein PG has the same meanings as in the compound of formula (I) above;
(c) deprotection of keto group of the compound of formula (V) to obtain the compound of formula (II-R);
or, alternatively, the steps (b) and (c) are substituted by the following steps:
(b1) deprotection of the keto group of the compound of formula (VI) to obtain the compound of formula (IV):

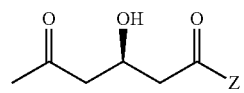

(c1) protection of the hydroxyl group of the compound of formula (IV) to obtain the compound of formula (II-R);
characterized in that the step (a), for both alternatives, is carried out by means of $NaBH_4$ and (+)-Tartaric acid, or, by means of a ketoreductase enzyme.

The above process for the preparation of the compound of formula (II-R) is summarized in the following scheme:

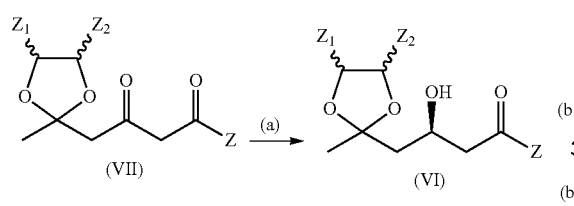
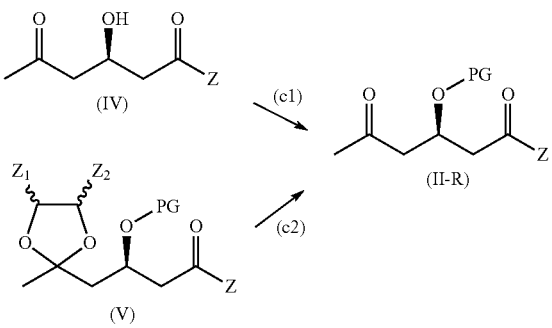

The conversion by means of a ketoreductase can be performed at:
pH comprised between 3-10,
concentration of the substrate comprised between 1-2000 mM,
temperature between 0-60° C., being preferred the range 25-40° C.,
buffers can be TRIS, MES, HEPES, etc.,
method for regeneration: Glucose dehydrogenase or alchooldehydrogenase,
Cofactor NADP+ or NAD+ on function of the selected enzyme.

The step (a) can be carried out with a ketoreductase enzyme, i.e. an enzyme able to reduce stereoselectively the carbonyl function to the hydroxyl function.

According to a more preferred embodiment, the step (a) of the process for the preparation of the compound of formula (II-R) is carried out by means of KRD-130 which is a ketoreductase enzyme. This enzyme indeed produces the best results since the conversion of the compound of formula (VII) to compound (VI) is quantitative and the enantiomeric excess is higher than 99.5%. KRD-130 is a ketoreductase enzyme commercially available provided by Codexis Inc. (200 Penobscot Drive, Redwood City, Calif. 94063).

According to an other preferred embodiment, the step (a) can be carried out with the enzyme 17beta-HSD5 recombinant murine indentified by SEQ. ID n.2 as disclosed in WO2011/000693.

The enzyme KRED-130 provides the best results in terms of conversion and e.e. for the enantioselective reduction of (VII) to (VI).

According to a preferred embodiment, the concentration of the cofactor NADP+ or NAD+ used is comprised in the range from 0.01 to 20 mM (mM=milliMolar), more preferably being about 1.5 mM.

When the process is carried out by means of a ketoreductase enzyme, $Z_1$ and $Z_2$ are, preferably, both hydrogen.

A preferred process for the process for the preparation of the compound of formula (II-R) by means of a ketoreductase enzyme, including the alternative steps (b1) and (c1) is summarized in the following scheme:

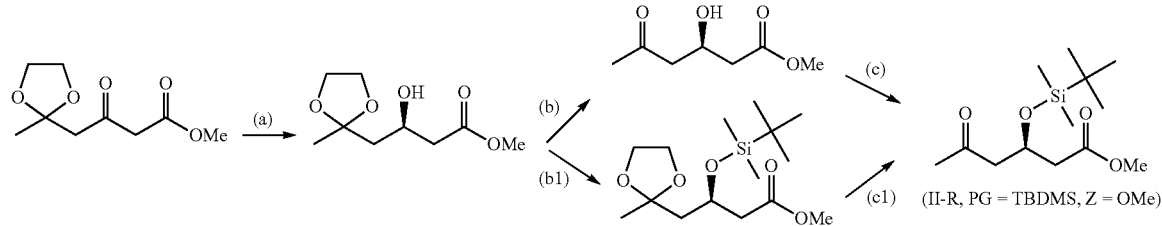

A more preferred process for the preparation of the compound of formula (II-R) by means of a ketoreductase enzyme is summarized in the following scheme:

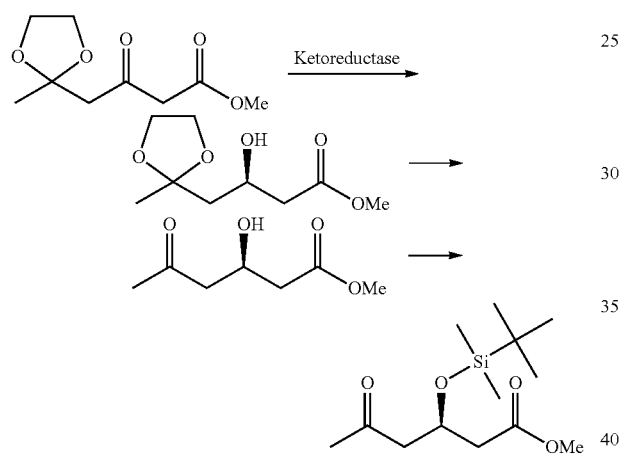

It is very important to underline that since the ketoreductase provide a compound with an extremely high enantiomeric excess, it is possible to obtain the following intermediates of the synthesis, such as the compound of formula (I) with a very high enentiomeric excess. This solve a very important problem related to the synthesis of the Statins, and Rosuvastain in particular, due to the presence of enantiomer and diasteromeric impurities in the statin product.

The step (a) of the process for the preparation of (II-R) can also be carried by means of $NaBH_4$ and (+)-Tartaric acid.

According to a preferred embodiment of the process for the preparation of the compound of formula (II-R) carried out by means of $NaBH_4$ and (+)-Tartaric acid, $Z_1$ and $Z_2$ are both (CO)OR, where R is equal or different and is selected between linear or branched $C_{1-7}$ alkyl, linear or branched $C_{1-7}$ alkenyl or alkynyl, $C_{3-7}$ cycloalkyl, aryl-$C_{0-4}$ alkyl, because when $Z_1$ and $Z_2$ are both (CO)OR instead hydrogen, the enantiomeric excess increases from 80% (see example 12) to 94%.

Indeed, when $Z_1$ and $Z_2$ are both (CO)OR and R is Methyl, Ethyl or benzyl, the correspondent compound of formula (VI) is prepared according to this process with an enantiomeric excess of 94%.

According to a preferred embodiments the carbons bringing the $Z_1$ and $Z_2$ group are optically active, in particular the following reaction scheme summarizes a preferred embodiment wherein an higher enantiomeric excess in the conversion of (VII) to (VI) is achieved:

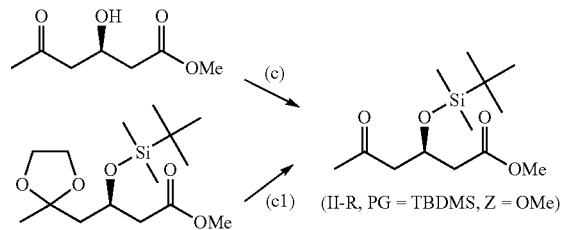

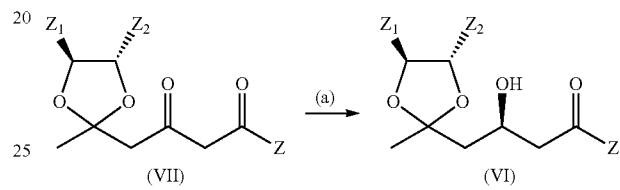

The compound of formula (VII) wherein $Z_1$ and $Z_2$ are both (CO)OR can be prepared by reaction of a gamma-beta diketoester with tartaric acid diesters, such as isopropyl, ethyl or benzyl esters.

The presence of (+)-Tartaric acid during the reduction reaction with $NaBH_4$ is essential to reach the compound (II) having R configuration.

The compound of formula (VII):

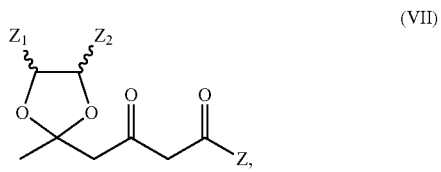

the compound of formula (VI):

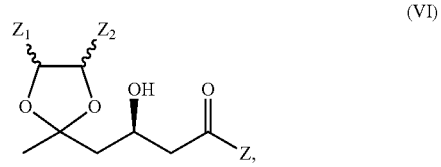

the compound of formula (V):

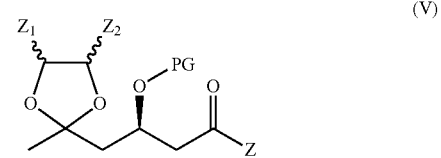

wherein PG and Z are the same as in the compound of formula (I) as defined above and $Z_1$ and $Z_2$ are equal or different and are (CO)OR, in which R is selected between linear or branched $C_{1-7}$ alkyl, linear or branched $C_{1-7}$ alkenyl or alkynyl, $C_{3-7}$ cycloalkyl, aryl-$C_{0-4}$ alkyl are thus useful intermediates for the preparation of the compound of formula (II-R).

A preferred process for the preparation of the compound of formula (I), including the preparation of the compound of formula (II), both having R configuration, is summarized in the following scheme:

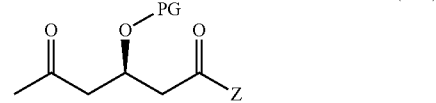

(II-R)

wherein PG and Z have the same meaning of as in the compound (I), has been found.

Such an alternative process for the preparation of the compound of formula (II-R):

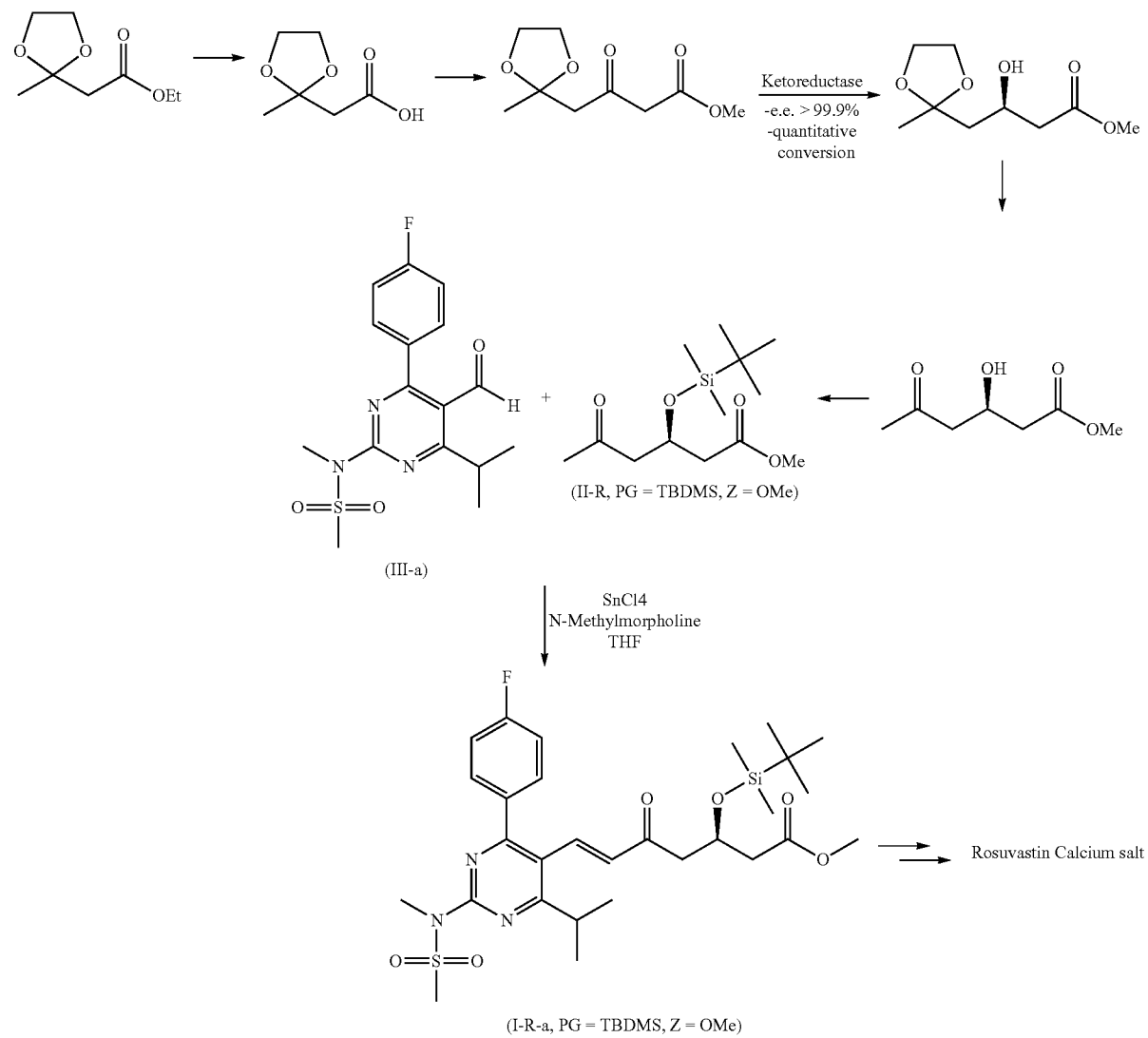

The high enantiomeric excess provided by the biotransformation carried out by the ketoreductase is beneficial for the whole synthesis since the enantiomeric and diastereomeric impurities of Rosuvastatin are avoided or drastically reduced.

Finally, an alternative process for the preparation of the compound of formula (II-R):

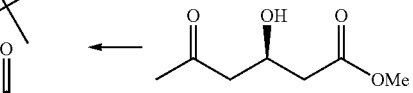

(II-R)

comprising the oxidation of the compound of formula (VIII-R):

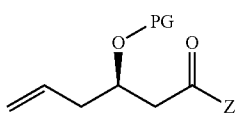
(VIII-R)

or, alternatively, comprising the following steps:
(a) the oxidation of the compound of formula (IX-R):

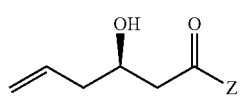
(IX-R)

to provide the compound of formula (X-R):

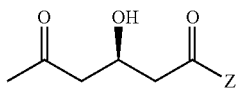
(X-R)

(b) protection of the hydroxyl group of the compound of formula (X-R) to give the compound of formula (II-R), wherein PG and Z have the same meaning of as in compound (I) above,
wherein the oxidation is carried out by an oxidant and in presence of a metal catalyst.

The process of direct conversion of the compound (VIII-R) to the compound (II-R) is preferred since provides higher molar yields and higher purity of the final product.

According the a preferred embodiment, the process for the preparation of compound of formula (II-R) is preferred wherein PG is TBDMS and Z is OMe.

The compound of formula (VIII-R) can be prepared according to the teaching e.g. of WO2011/124050, while the preparation of the compound of formula (IX-R) is well disclosed in many scientific publications.

According to a preferred embodiment the oxidation is performed in presence of a Palladium compound as metal catalyst and the oxidant is air or an hydroperoxide.

According to a preferred embodiment, the first set of preferred conditions sees: Palladium compound being Palladium (II) chloride or acetate, the oxidant being air, and further comprising CuCl or Cu(OAc)$_2$.

Copper compounds can be added in amount comprised between 0.1 to 3.0 molecular equivalents, being preferred from 0.2 to 0.5 molecular equivalents.

The product of formula (II-R) prepared under these conditions contains, as side-product, about 15% of the aldehyde having the following structure:

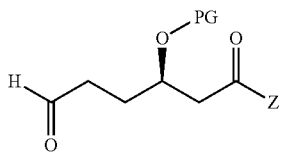

into the final product.

The product of the reaction thus obtained can be purified by means of the formation of bisulfitic adduct of the side-product, followed by distillation under vacuum of the product.

The purification of the product of the reaction through the formation of the bisulfitic adduct can be performed using a mixture of water/Methanol/Methyl-THF/1:1:5) as solvent and with NaHSO$_3$ (0.3 equiv. in 1 Vol. Water), filtration and further washings with water.

AcOEt can be used instead of Methyl-THF achieving similar results. The product thus prepared can be distilled at 5 mbar and 140° C. thus providing the compound of formula (II-R, PG=TBDMS, Z=OMe) as a colourless oil free from the aldehyde by-product.

Using the first set of preferred conditions, the oxidation is carried out in mixture of an organic solvent, such as e.g. DMF, THF, Dioxane and Water.

The preferred ratio Organic solvent:water is 7:1 (volume/volume).

The reaction can be carried out in a range of temperature comprised from about 0° C. to about 60° C. At 25° C. the reaction is completed in about 48 hours. The temperature about 25° C. is preferred because provides higher molar yields.

The palladium compound is typically employed in catalytic amounts, i.e. from 0.01 to 0.20 molecular equivalents. The more preferred amount of Palladium catalyst is 0.10 molecular equivalents.

When the first set of conditions is used, the molar yield of the process is quantitative but, after purification of the product, the molar yield is not higher than 70-80%.

According to a more preferred embodiment, the second set of preferred conditions to perform the oxidation sees the presence of a Palladium compound as metal catalyst and an hydroperoxide as oxidant.

Using these conditions the oxidation reaction provides exclusively the compound of formula (II-R).

According to a preferred embodiment the Palladium compound is Palladium (II) acetate.

The hydroperoxide oxidant is chosen between cumene hydroperoxyde, cyclohexylhydroperoxyde, t-buthylhydroperoxyde (t-BuOOH or Tert-BuOOH), being preferred t-buthylhydroperoxyde.

According to a more preferred embodiments, the Palladium compound is Palladium (II) acetate and the hydroperoxide oxidant is Tert-butylhydroperoxyde.

Using the second set of preferred conditions, the oxidation is carried out in an organic solvent, such as e.g. Toluene.

The product of the reaction can also be purified according to the procedure described for the first set of conditions, thus removing the excess of t-Butylhydroperoxyde.

The palladium compound is typically employed in catalytic amounts, i.e. from 0.01 to 0.20 molecular equivalents. The more preferred amount of Palladium catalyst is 0.10 molecular equivalents.

The reaction can be carried out in a range of temperature comprised from about 40° C. to about 80° C. At 60° C. the reaction is completed in about 24 hours.

When the second set of conditions is used, the molar yield of the process is quantitative or almost quantitative and the oxidation is highly regioselective since only the product of formula (II-R) is generated without any traces of the aldehyde by-product.

The process according to the following scheme

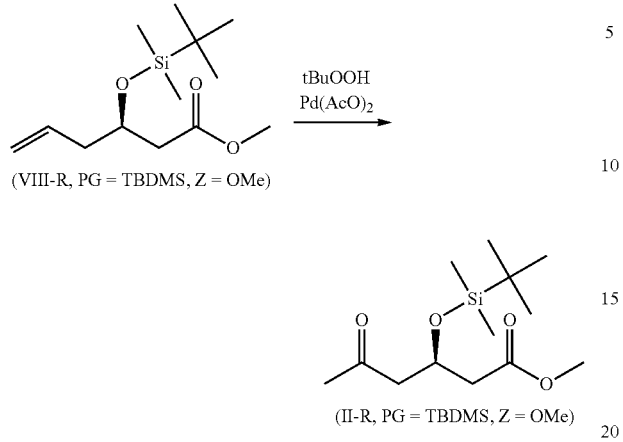

is preferred since provides the best conversions, yields, and the highest purity of the final product.

EXPERIMENTAL SECTION

The starting material Pentanedioic acid, 3-[[(1,1-dimethylethyl) dimethylsilyl]oxy]-, 1-methyl ester, (3R)— also called J4 and having RN 109744-49-2 is largely commercially available (e.g. by Hangzhou APIChem Technology Co., Ltd.).

Example 1

Synthesis of the compound of formula (II) in which PG is TBDMS and Z is O-t-Butyl (compound J4d)

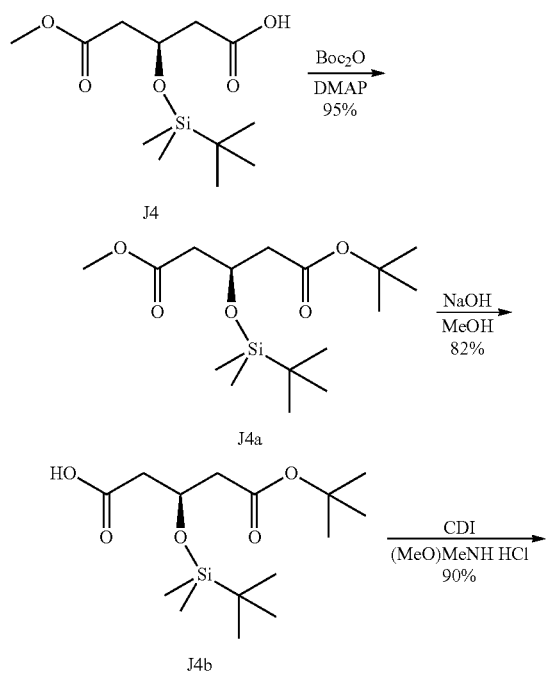

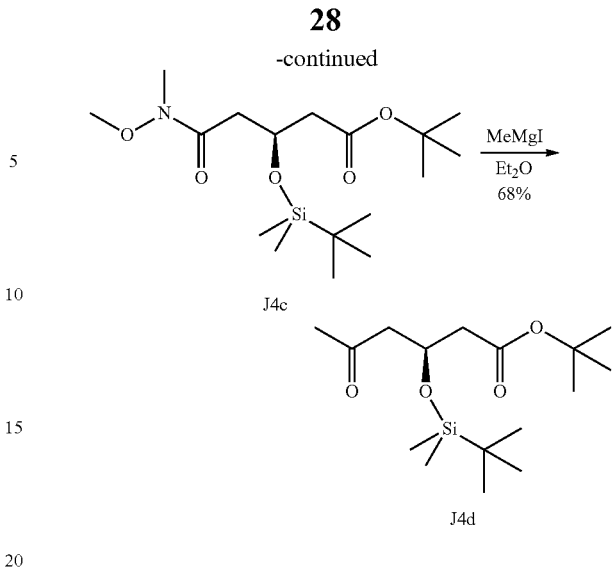

Preparation of (S)-1-tert-butyl 5-methyl 3-(tert-butyldimethylsilyloxy) pentanedioate (of formula J4a)

To a solution of J4 (16.58 g, 60 mmol) in methylene chloride (80 ml) was added N-methyl morpholine (7.92 mL, 72 mmol) at 0° C. and the reaction was maintained for 15-30 minutes, followed by slow addition of BOO anhydride (22.05 mL, 96 mmol) in methylene chloride (60 ml) at 0° C. The reaction was maintained for 15-30 minutes. N,N-dimethylaminopyridine (366 mg, 3 mmol) was added at 0° C., and the mass was maintained at 25-30° C. for 3-5 hours. Silica gel (4.2 g) was added, followed by removal of silica gel. Water (50 ml) was added to the reaction mass and the pH was adjusted to 4-4.5 using 1M hydrochloric acid. The aqueous phase was separated and the organic phase was washed with water, followed by removal of methylene chloride under vacuum, giving the compound of formula J4a (19.8 g, 99% yield) as a brown oil.

Preparation of (S)-5-tert-butoxy-3-(tert-butyldimethylsilyloxy)-5-oxopentanoic acid (of formula J4b)

Compound of formula J4a (18 g, 54.1 mmol) was dissolved in methanol (100 mL) and NaOH 4M (50 mL) was added. After stirring for 24 hrs at room temperature, the mixture was neutralized with HCl 1M and extracted with cyclohexane (3×100 mL). Combined organic extracts were washed with $H_2O$ (50 mL), saturated aqueous NaCl (50 mL), dried over anhydrous $MgSO_4$ and concentrated in vacuum to give product J4b (14.1 g, 82% yield) as a brown oil.

Preparation of (S)-tert-butyl-3-(tert-butyldimethylsilyloxy)-5-(methoxy (methyl)amino)-5-oxopentanoate (of formula J4c)

To a solution of J4b (12.7 g, 39.9 mmol) in methylene chloride (100 ml) was slowly added 1,1'-carbonyldiimidazole (7.76 g, 47.9 mmol) and stirred at room temperature for 15 minutes until $CO_2$ ceases. N,O-dimethylhydroxylamine hydrochloride (5.60 g, 57.4 mmol) was added and the mixture was stirred overnight. Water (50 mL) was added and the mixture was extracted with DCM (2×50 mL). Combined organic extracts were washed with $H_2O$ (50 mL), saturated aqueous NaCl (50 mL), dried over anhydrous MgSO₄ and concentrated in vacuum to give product J4c (13.5 g, 90% yield) as a brown oil.

Preparation of (S)-tert-butyl 3-(tert-butyldimethylsilyloxy)-5-oxohexanoate (of formula J4d)

To a stirred solution of J4c (2.5 g, 6.9 mmol) in THF (20 mL) was added MeMgI (10 mL, 15.2 mmol, 1.52 M in Et₂O) at 0° C. and the mixture was stirred at room temperature for 5 hrs. The reaction was quenched with satd. NH₄Cl (aq) and extracted with Et₂O (3×20 mL). Combined organic extracts were washed with H₂O (20 mL), saturated aqueous NaCl (20 mL), dried over MgSO₄ and concentrated in vacuum. The crude product was purified by silica gel chromatography (eluent hexane/Et₂O in gradient from 10:0 to 7:3) affording the corresponding product J4d (1.51 g, 69% yield) as a colorless oil.

$^1$H-NMR (200 MHz, CDCl₃) d: 4.50 (quintet, J=6.1 Hz, 1H), 2.68 (d, J=6.1 Hz, 2H), 2.40 (d, J=6.1 Hz, 2H), 2.15 (s, 3H), 1.43 (s, 9H), 0.85 (s, 9H), 0.06 (d, J=6.1 Hz, 6H) ppm.

Example 2

Synthesis of the compound of formula (I-a) in which PG is TBDMS and Z is O-t-Bu (with S-configuration).

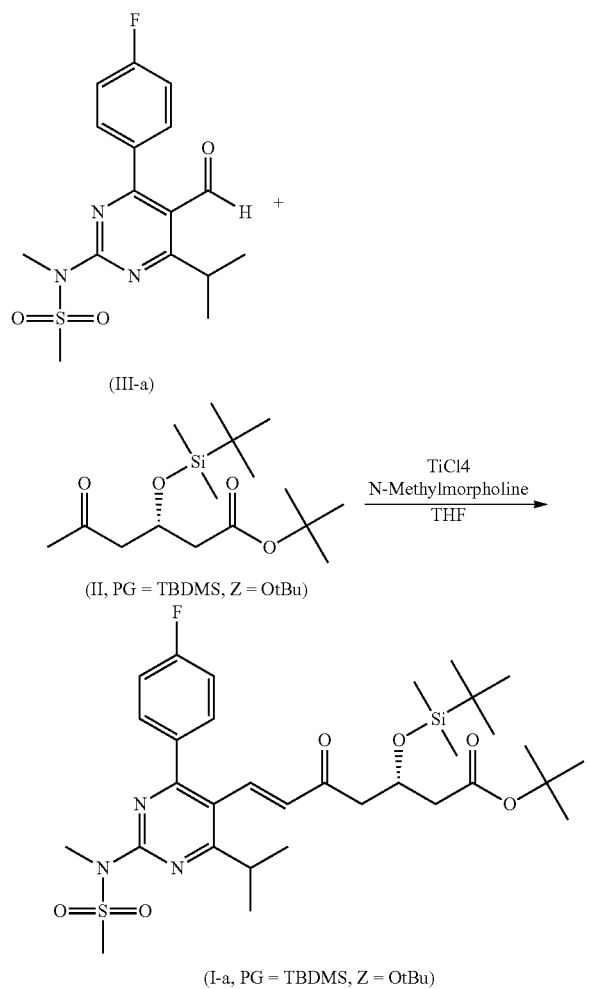

A solution of titanium tetrachloride 1M (0.6 mL) was added to 2 mL of cold (0° C.) tetrahydrofuran. After the mixture was stirred an additional 15 minutes, a solution of N-[4-(4-fluorophenyl)-5-formyl-6-(propan-2-yl) pyrimidin-2-yl]-N-methylmethanesulfonamide (compound (III-a)) (105 mg, 0.3 mmol) in 1 mL of tetrahydrofuran and a solution of J4d (95 mg, 0.3 mmol) (prepared according to example 1) in 1 mL of tetrahydrofuran were slowly added in sequence. A solution of 0.25 ml of N-methylmorpholine in 1 mL of tetrahydrofuran was then added dropwise and the mixture was stirred at rt overnight. Water (20 mL) was added and the mixture was extracted with EtOAc (3×20 mL). Combined organic extracts were washed with H₂O (20 mL), saturated aqueous NaCl (20 mL), dried over MgSO₄ and concentrated in vacuum. The crude product was purified by silica gel chromatography (eluent hexane/AcOEt in gradient from 9:1 to 7:3) affording the corresponding product of formula (I-a; PG=TBDMS, R=OtBu) (53.3 mg, 27% yield).

$^1$H-NMR (200 MHz, CDCl₃) d: 7.56-7.65 (m, 3H), 7.11 (t, J=8.5 Hz, 2H), 6.16 (d, J=16.5 Hz, 1H), 4.54 (quintet, J=5.7 Hz, 1H), 3.58 (s, 3H), 3.51 (s, 3H), 3.37 (quintet, J=6.7 Hz, 1H) 2.75 (d, J=6.1 Hz, 2H), 2.40 (d, J=6.1 Hz, 2H), 1.43 (s, 9H), 1.29 (d, J=6.7 Hz, 6H), 0.82 (s, 9H), 0.04 (d, J=11.6 Hz, 6H) ppm.

This compound can be useful for the preparation of the Rosuvastatin S-enantiomer or related diastereoisomers which are important reference standards to control the synthesis of Rosuvastatin with particular reference to the optical purity of the product.

Example 3

Synthesis of the compound of formula (II) in which PG is TBDMS and Z is OMe (compound (R)-J4K).

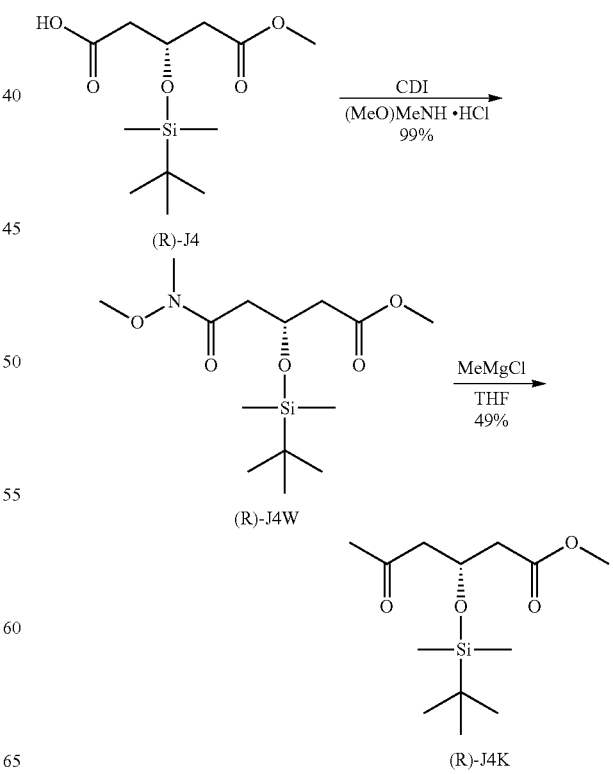

Preparation of (R)-methyl 3-(tert-butyldimethylsilyloxy)-5-(methoxy(methyl)amino)-5-oxopentanoate ((R)-J4W): to a solution of J4 (in the scheme it is named as (R)-J4) (20.0 g, 72.4 mmol) in methylene chloride (120 ml), 1,1'-carbonyldiimidazole (14.08 g, 86.8 mmol) was slowly added and stirred at room temperature for 15 minutes until $CO_2$ ceases. N,O-dimethylhydroxylamine hydrochloride (8.82 g, 90.4 mmol) was added and the mixture was stirred overnight. Water (50 mL) was added and the mixture was extracted with DCM (2×50 mL). Combined organic extracts were washed with $H_2O$ (50 mL), saturated aqueous NaCl (50 mL), dried over $MgSO_4$ and concentrated in vacuum to give product (R)-J4W (22.9 g, 99% yield) as a colorless oil.

Preparation of (R)-methyl 3-(tert-butyldimethylsilyloxy)-5-oxohexanoate ((R)-J4K): to a stirred solution of (R)-J4W (4.79 g, 15 mmol) in THF (30 mL), MeMgCl (7.5 mL, 22.5 mmol, 3 M in THF) was added at 0° C. and the mixture was stirred for 4 hrs at 0° C. The reaction was quenched with satd. $NH_4Cl$ (aq) and extracted with $Et_2O$ (3×30 mL). Combined organic extracts were washed with $H_2O$ (20 mL), saturated aqueous NaCl (20 mL), dried over $MgSO_4$ and concentrated in vacuum. The crude product was purified by silica gel chromatography (eluent hexane/$Et_2O$ in gradient from 10:0 to 7:3) affording the corresponding product (R)-J4K (2.01 g, 49% yield) as a colorless oil.

$^1$H-NMR (200 MHz, $CDCl_3$) d: 4.56 (quintet, J=6.1 Hz, 1H), 3.66 (s, 3H), 2.68 (dd, J=6.1, 1.4 Hz, 2H), 2.50 (dd, J=6.1, 3.3 Hz, 2H), 2.16 (s, 3H), 0.84 (s, 9H), 0.06 (d, J=3.9 Hz, 6H) ppm.

Example 4

Synthesis of the compound of formula (I-a) in which PG is TBDMS and Z is OMe (with R-configuration).

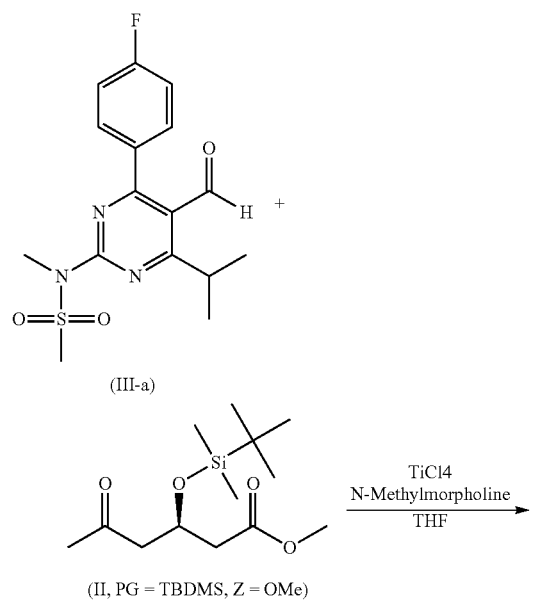

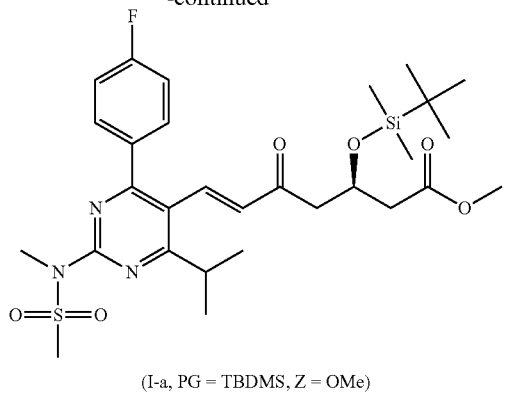

To a solution of N-[4-(4-fluorophenyl)-5-formyl-6-(propan-2-yl) pyrimidin-2-yl]-N-methylmethanesulfonamide (compound (III-a)) (105 mg, 0.3 mmol) in 3 mL of tetrahydrofuran at 0° C. was slowly added a solution of titanium tetrachloride 1M in dichloromethane (0.6 mL, 0.6 mmol). After the mixture was stirred 15 minutes, a solution of (R)-J4K (98.8 mg, 0.36 mmol) (as prepared in the previous experiment) in 1 mL of tetrahydrofuran was slowly added. A solution of N-methylmorpholine (0.13 mL, 1.2 mmol) in 1 mL of tetrahydrofuran was then added dropwise and the mixture was stirred at 0° C. for 3 hrs. Water (20 mL) was added and the mixture was extracted with EtOAc (3×20 mL). Combined organic extracts were washed with $H_2O$ (20 mL), saturated aqueous NaCl (20 mL), dried over $MgSO_4$ and concentrated in vacuum. The crude product was purified by silica gel chromatography (eluent hexane/$Et_2O$ in gradient from 9:1 to 6:4) affording the corresponding product of formula (I-a; PG=TBDMS, Z=OMe) (115 mg, 63% yield).

$^1$H-NMR (200 MHz, $CDCl_3$) d: 7.57-7.65 (m, 3H), 7.11 (t, J=8.5 Hz, 2H), 6.16 (d, J=16.5 Hz, 1H), 4.60 (quintet, J=6.1 Hz, 1H), 3.66 (s, 3H), 3.58 (s, 3H), 3.51 (s, 3H), 3.36 (quintet, J=6.7 Hz, 1H) 2.74 (dd, J=5.5 Hz, 1.8H), 2.49 (dd, J=6.1 Hz, 1.2; H), 1.29 (d, J=6.7 Hz, 6H), 0.81 (s, 9H), 0.03 (d, J=9.2 Hz, 6H) ppm.

This compound is an important intermediate of the synthesis of Rosuvastatin. The conversion of this compound to Rosuvastatin is disclosed in EP521471.

Example 5

Synthesis of the compound of formula (I-c) in which PG is TBDMS and Z is OMe (with R-configuration).

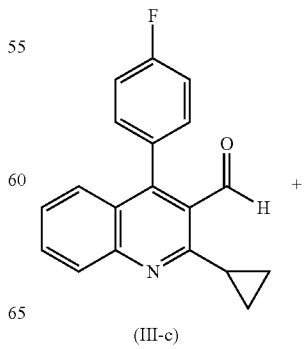

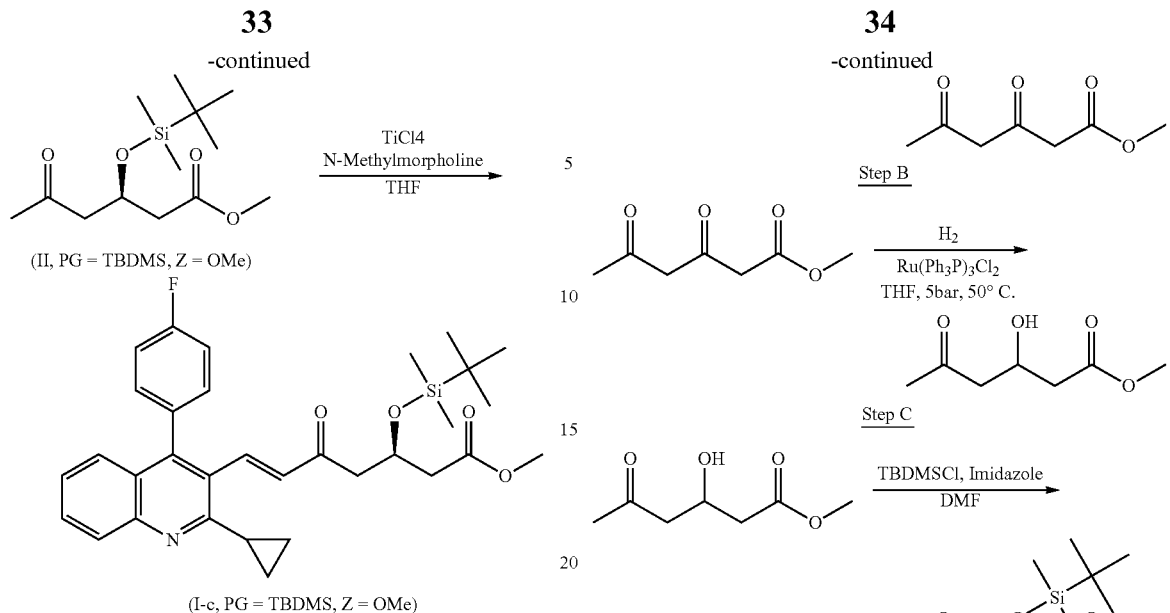

To a solution of 2-cyclopropyl-4-(4-fluorophenyl)quinoline-3-carbaldehyde (compound of formula (III-c); commercially available) (146 mg, 0.5 mmol) in 5 mL of Tetrahydrofuran at 0° C. was slowly added a solution of titanium tetrachloride 1M in dichloromethane (1.0 mL, 1.0 mmol). After the mixture was stirred 15 minutes, a solution of (R)-J4K (165 mg, 0.6 mmol) (compound of formula (II, PG=TBDMS, Z=OMe) with R configuration, as prepared in Example 3) in 1 mL of tetrahydrofuran was slowly added. A solution of N-methylmorpholine (0.22 mL, 2 mmol) in 1 mL of tetrahydrofuran was then added dropwise and the mixture was stirred at 0° C. for 3 hours. Water (20 mL) was added and the mixture was extracted with EtOAc (3×20 mL). Combined organic extracts were washed with $H_2O$ (20 mL), saturated aqueous NaCl (20 mL), dried over $MgSO_4$ and concentrated in vacuum. The crude product was purified by silica gel chromatography (eluent hexane/$Et_2O$ in gradient from 9:1 to 6:4) affording the corresponding compound of formula (I-c, PG=TBDMS, Z=OMe) having R configuration (192 mg, 70% yield).

$^1$H-NMR (200 MHz, $CDCl_3$) d: 7.99 (d, J=8.5 Hz, 1H), 7.67 (d, J=16.5 Hz, 1H), 7.66 (m, 1H), 7.22-7.40 (m, 6H), 6.37 (d, J=16.5 Hz, 1H), 4.60 (quintet, J=5.8 Hz, 1H), 3.69 (s, 3H), 2.73 (dd, J=6.1 Hz, 2.4; H), 2.50 (dd, J=6.1 Hz, 3.7; H), 2.39 (m, 1H), 1.43 (m, 2H), 1.10 (m, 2H), 0.84 (s, 9H), 0.05 (d, J=10.4 Hz, 6H) ppm.

This compound is an important intermediate of Pitavastatin since after the removal of the hydroxyl protecting group and the carbonyl group is reduced diastereoselectively and then the Pitavastatin ester is hydrolized to Pitavastatin.

Example 6

Synthesis of the compound of formula (I-a) in which PG is TBDMS and Z is OMe (in racemic form).

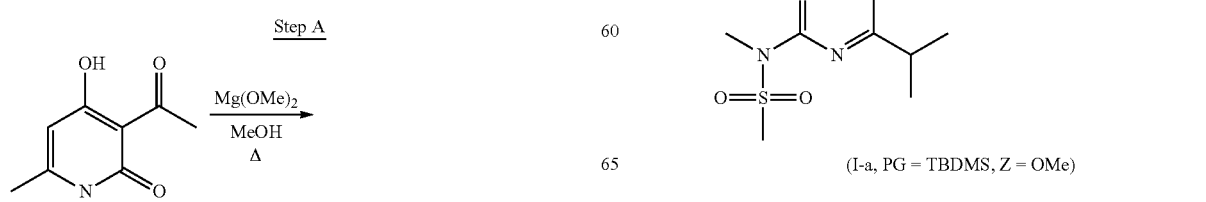

Step A: Magnesium methoxide (6% in MeOH, 530 mL) was added to a suspension of dehydroacetic acid (31 g) in methanol (600 mL) at room temperature. The reaction mixture was refluxed and stirred for 5 h. The solvent was removed and the residue dissolved in HCl 1M (1.5 L). The aqueous phase was extracted with EtOAc (2×750 mL) and then the solvent was evaporated under reduced pressure to give a yellow oil, which was filtered on a silica cartridge using dichloromethane as eluent. After the solvent removal, methyl 3,5-dioxohexanoate was obtained as a light yellow oil (19.9 g).

Step B: Methyl 3,5-dioxohexanoate(19.0 g) was dissolved in THF (380 mL) and tris(triphenylphosphine) ruthenium (II) dichloride (1.1 g) was added. The reaction mixture was hydrogenated at 5 bar, 50° C. for 16 h and then cooled to room temperature. The solvent was removed under vacuum and the oil was purified on silica gel (hexane/EtOAC 1:1) to give the final methyl 3-hydroxy-5-oxohexanoate (10 g).

Step C: Methyl 3-hydroxy-5-oxohexanoate(10 g) was dissolved in dry DMF (250 mL) and the solution was cooled down to 0° C. Imidazole (8.5 g) and tert-butyldimethylsilyl chloride (11.3 g) were added. The reaction mixture was stirred at 25° C. for 12 h and then quenched with a 10% NaHCO₃ solution. After the extraction with toluene (3×250 mL), the collected organic phase was dried under vacuum and the resulted oil was purified via chromatographic column on silica gel (hexane/EtOAc 9:1). Methyl 3-(tert-butyldimethylsiloxy)-5-oxohexanoate (compound of formula (II, PG=TBDMS, Z=OMe)) being a racemic compound) was obtained as a yellow oil (9.1 g, 53% yield).

Step D: Titanium tetrachloride (1M in dichloromethane, 12.67 mL) was added dropwise to a solution of 4-(4-fluorophenyl)-6-isopropyl-2-(N-methyl-N-methylsulfonylamino)-5-pyrimidinecarbardehyde (2.13 g) (compound of formula (III-a)) in dry THF (60 mL) at 0° C. After stirring for 15 minutes, a solution of compound of formula (II, PG=TBDMS, Z=OMe) (2 g) in dry THF (20 mL) and subsequently a solution of N-methylmorpholine (2.64 mL) in dry THF (20 mL) were slowly added. The reaction mixture was stirred at 0° C. for 3 h, then quenched with water (40 mL) and extracted with EtOAc (3×40 mL). The combined organic layers were dried under vacuum and the resulting oil was purified via chromatographic column on silica gel (hexane/EtOAc 9:1) to give the 2.5 g of the corresponding racemic product of formula (I-a, PG=TBDMS, Z=OMe) (Molar yield=68% yield).

The ¹H-NMR spectrum is the same of that of the product of Example 4.

Example 7

Synthesis of the compound of formula (I-a) in which Z is OMe but without protecting group (in racemic form).

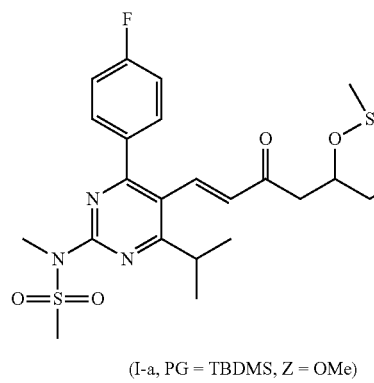

(I-a, PG = TBDMS, Z = OMe)

HF aq.

-continued

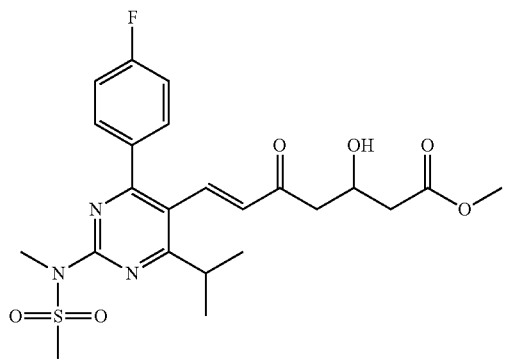

To a solution of the compound of formula (I-a, PG=TBDMS, Z=OMe) (2.0 g) in acetonitrile (19 mL) at 0° C. a solution of hydrogen fluoride (1.9 mL) in acetonitrile (5 mL) is added dropwise. The reaction mixture is warmed up to room temperature and stirred for 3 h, then neutralized with sodium hydroxide till pH=6 and filtered. The solution is concentrated under vacuum to remove all the acetonitrile; the residue is taken up with MTBE (20 mL) and washed with a sodium bicarbonate solution (10 mL). The organic layer is the concentrated under reduced pressure to give the desired product.

This compound can be converted in racemic Rosuvastatin by means of the carbonyl reduction followed by hydrolisys of the ester function.

Example 8

Synthesis of the compound of formula (I-a) in which PG is TBDMS and Z is OMe (with R-configuration)—Aldol conditions screening

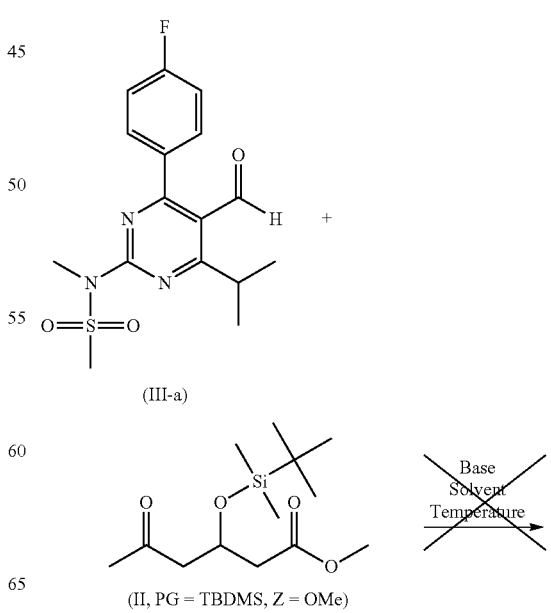

(III-a)

(II, PG = TBDMS, Z = OMe)

-continued

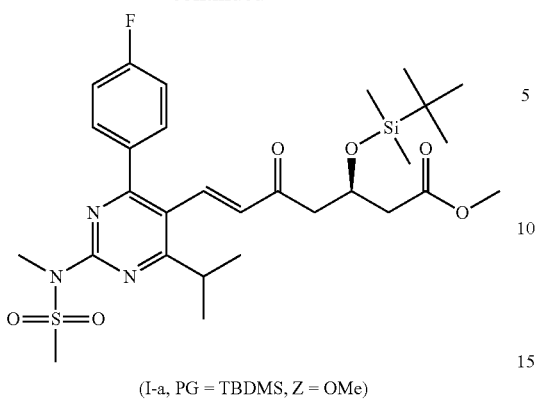

(I-a, PG = TBDMS, Z = OMe)

The example 4 was repeated without the Lewis acid and testing the following bases, solvents, temperature and amounts of base:

Bases: LiOH, NaOH, KOH, $K_2CO_3$, Amine;

Solvents: MeOH, MeCN, THF, Toluene;

Temperature: Room temperature, Reflux.

Amount of bases: catalytic or stoichiometric.

All the experiments failed since the target compound was not formed in appreciable amounts.

Example 9

Synthesis of the compound of formula (I-a) in which PG is TBDMS and Z is OMe (with R-configuration)—Lewis Acid/Base screening

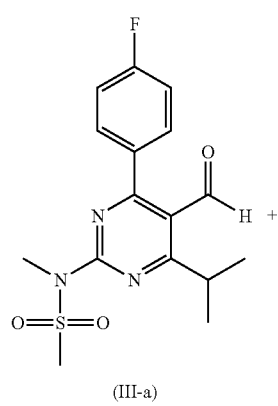

(III-a)

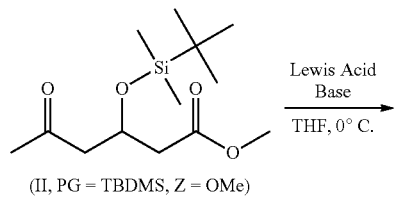

(II, PG = TBDMS, Z = OMe)

-continued

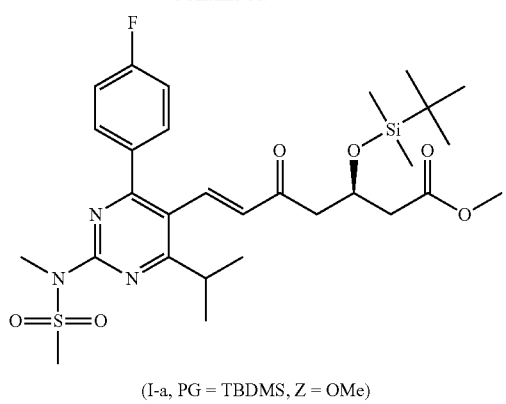 [SMILES: COC(=O)CC(CC(=O)/C=C/c1c(-c2ccc(F)cc2)nc(N(C)S(C)(=O)=O)nc1C(C)C)O[Si](C)(C)C(C)(C)C]

(I-a, PG = TBDMS, Z = OMe)

The Example 4 was repeated changing the Lewis acid, the base and the amounts of acid and base used. The following comparative table resumes the results of 10 experimental trials. The yields are calculated by NMR.

TABLE 1

| entry | Lewis Acid (Eq) | Base (eq.) | Yield (%) |
| --- | --- | --- | --- |
| 1 | $TiCl_4$ (0.5) | N-methylmorpholine (1) | 24 |
| 2 | $TiCl_4$ (1) | N-methylmorpholine (2) | 48 |
| 3 | $TiCl_4$ (2) | N-methylmorpholine (4) | 79 |
| 4 | / | N-methylmorpholine (4) | 0 |
| 5 | $FeCl_3$ (2) | N-methylmorpholine (4) | 21 |
| 6 | $AlCl_3$ (2) | N-methylmorpholine (4) | 76 |
| 7 | $TiCl_4$ (2) | Triethylamine (4) | 78 |
| 8 | $TiCl_4$ (2) | DABCO (4) | 75 |
| 9 | $TiCl_4$ (2) | Ethyldiisopropylamine (4) | 76 |
| 10 | $TiCl_4$ (2) | TMEDA (4) | 66 |

Example 10

Direct synthesis of the compound of formula (I-a) without PG and where Z is OMe (with R-configuration)—comparative examples not part of the present invention.

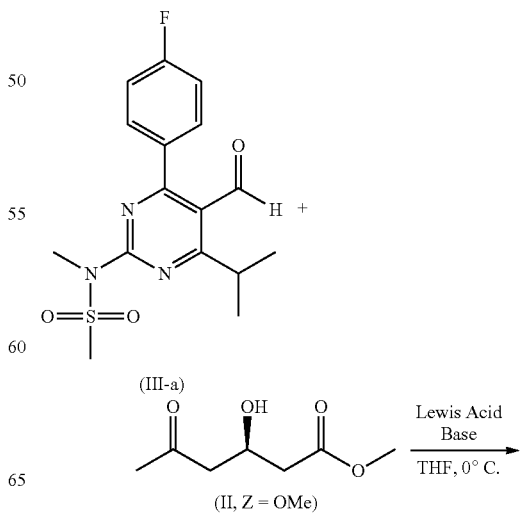

-continued

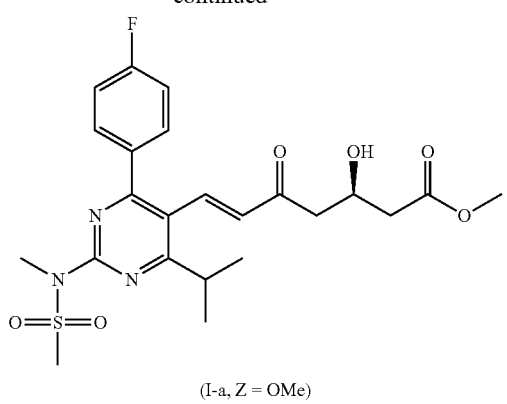

(I-a, Z = OMe)

The Example 4 was repeated but using the compound of formula (II) without the protection on the hydroxyl group. The reaction conditions were studied changing Lewis acid, the base and the amounts compound (II) (Ketoalcohol) used. The amount of base was double of that of the Lewis acid in terms of molar equivalents. The following comparative table resumes the results of 8 experimental trials.

TABLE 2

| entry | Eq. Ketoalcohol | Lewis Acid | Base | Yield (%) |
|---|---|---|---|---|
| 1 | 1 | TiCl$_4$ | N-methylmorpholine | 5 |
| 2 | 3 | TiCl$_4$ | N-methylmorpholine | 8 |
| 3 | 3 | AlCl$_3$ | N-methylmorpholine | 28 |
| 4 | 3 | AlCl$_3$ | Triethylamine | 35 |
| 5 | 3 | AlCl$_3$ | DABCO | 22 |
| 6 | 3 | AlCl$_3$ | Ethyldiisopropylamine | 41 |
| 7 | 3 | AlCl$_3$ | TMEDA | 41 |
| 8 | 4.5 | AlCl$_3$ | Ethyldiisopropylamine | 45 |

This reaction provides poor yields.

Example 11

Synthesis of the compound of formula (I-a) in which PG is TBDMS and Z is OMe (in racemic mixture)—using SnCl$_4$ as Lewis acid.

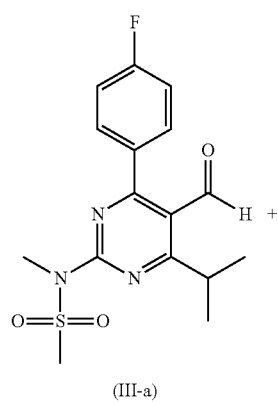

(III-a)

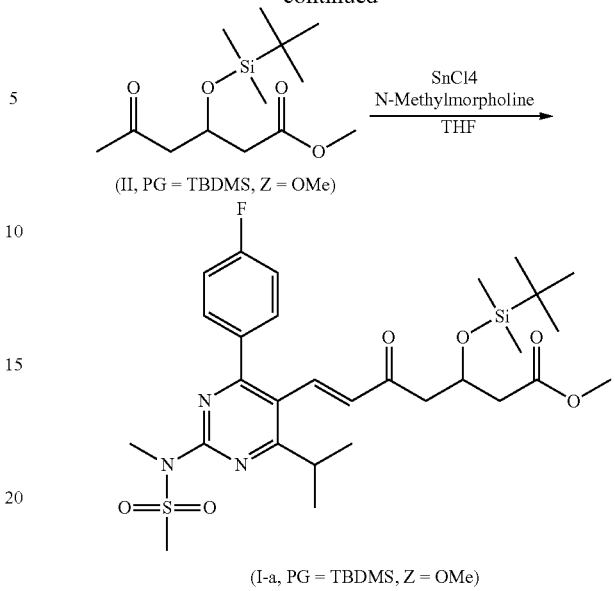

(I-a, PG = TBDMS, Z = OMe)

Tin tetrachloride (1M in dichloromethane, 12.67 mL) was added dropwise to a solution of 4-(4-fluorophenyl)-6-isopropyl-2-(N-methyl-N-methylsulfonylamino)-5-pyrimidinecarbardehyde (2.13 g) in dry THF (11 mL) at 0° C. After stirring for 15 minutes, a solution of compound of formula (II) wherein the hydroxyl protecting group is t-Butyl dimethyl silyl (TBDMS) and Z is OMe (2.5 g, 1.5 eq.) (as prepared in step C of Example 6) in dry THF (18 mL) was slowly added followed by the addition of a solution of N-methylmorpholine (1.99 mL, 3 eq.) in dry THF (18 mL) in 1.5 h. The reaction mixture was stirred at 0° C. for 1.5 h, then quenched with water (10 mL). Subsequently a saturated solution of Rochelle salts (30 mL) was added together with 10% NaHCO$_3$ solution (30 mL) and isopropyl acetate (50 mL). The mixture was stirred vigorously for 1 h and then the layers were separated. The organic phase was washed with brine (20 mL) and dried under vacuum. The oil was purified via chromatographic column on silica gel (hexane/EtOAc 9:1) to give the final product of formula (I-a) in racemic form (3.0 g, 81% yield).

Similar results have been achieved starting from 20 g of compound (III-a) through the same procedure of example 11.

Example 12

Synthesis of compound of formula (II-R).

Step a: Synthesis of (2-methyl-1,3-dioxolan-2-yl)acetic acid (1)

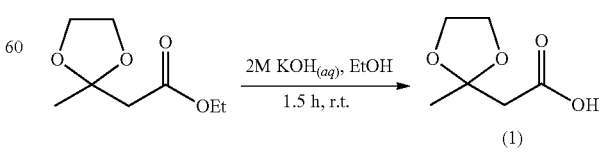

In a 250 ml 1 necked round bottom flask, ethyl 2-(2-methyl-1,3-dioxolan-2-yl) acetate (15 g, 86.11 mmol, 1 eq)

was dissolved in EtOH (75 ml). An aqueous solution of KOH 2M (64.6 ml, 126.16 mmol, 1.5 eq) was then added dropwise. The reaction was left under stirring at r.t. for 1.5 h, then EtOH was removed using a rotavap. The aqueous phase was washed with MTBE (2×25 ml), and the pH was brought to 3 using HCl 2M. The phase was extracted with AcOEt (6×50 ml). The pooled organic fractions were dried over MgSO$_4$ and the solvent was removed under reduced pressure giving 11.68 g (93%) of colourless oil (compound of formula (1)).

Step b: Synthesis of methyl 4-(2-methyl-1,3-dioxolan-2-yl)-3-oxobutanoate (2)

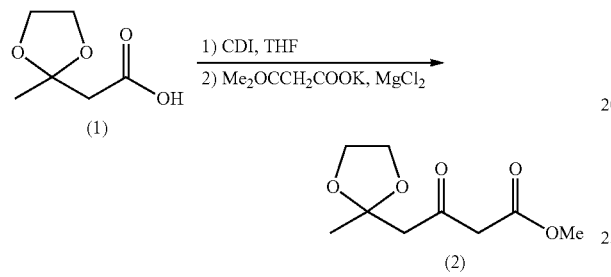

In a 4 necked 250 ml round bottom flask kept under Ar atmosphere, intermediate (1) (11.68 g, 79.92 mmol, 1 eq) was dissolved in dry THF (50 ml), CDI (15.55 g, 95.91 mmol, 1.2 eq) was then added and the mixture was left under stirring at r.t. for 1 h. In a second 4 necked 250 ml round bottom flask kept under Ar atmosphere, potassium monomethylmalonate (14.98 g, 95.91 mmol, 1.2 eq) and magnesium chloride (95.91 mmol, 1.2 eq.) were suspended in THF (50 ml), the mixture was left under stirring at r.t. for 30 min.

The solution contained in the first flask was then added in one portion to the suspension contained in the second flask. After 1 night under vigorous stirring, the mixture was poured in a cold HCl 1M solution. The aqueous solution was extracted with 4×100 ml AcOEt, dried over MgSO$_4$ and the solvent was removed under reduced pressure. The obtained product was purified using a 300 g SiO$_2$ cartridge, eluting with Cy/AcOEt. From 9:1 to 8:2. The pooled fractions gave 9.69 g (60%) of (2) as a colourless oil.

Step c: Synthesis of methyl-(3R)-3-hydroxy-4-(2-methyl-1,3-dioxolan-2-yl) butanoate (3)

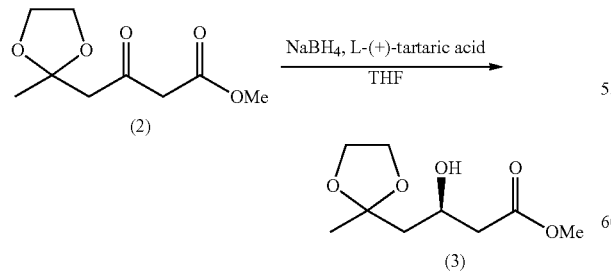

In a 3 necked 100 ml RBF kept under Ar atmosphere, L-(+)-tartaric acid (1.48 g, 9.89 mol, 4 eq) was added to a suspension of NaBH$_4$ (374 mg, 9.89 mol, 4 eq.) in THF (30 ml). The mixture was refluxed for 4 h, then cooled to r.t. and then to −20° C. Intermediate (2) (500 mg, 2.47 mol, 1 eq) dissolved in THF (2 ml) was added dropwise keeping T<−10° C. The mixture was left under stirring for 1 h at −10° C. and overnight at −18° C.

Water (50 ml) was then added to the reaction. The aqueous phase was extracted with DCM (3×50). The pooled organic fractions were dried over MgSO$_4$ and the solvent was removed under reduced pressure. The obtained product was purified using a 100 g SiO$_2$ cartridge, eluting with 7:3 Cy/AcOEt giving 0.36 g (71%) of (3) as a colourless oil (ee 80%).

Example 13

Synthesis of dimethyl (4R,5R)-2-[(2R)-2-hydroxy-4-methoxy-4-oxobutyl]-2-methyl-1,3-dioxolane-4,5-dicarboxylate (5).

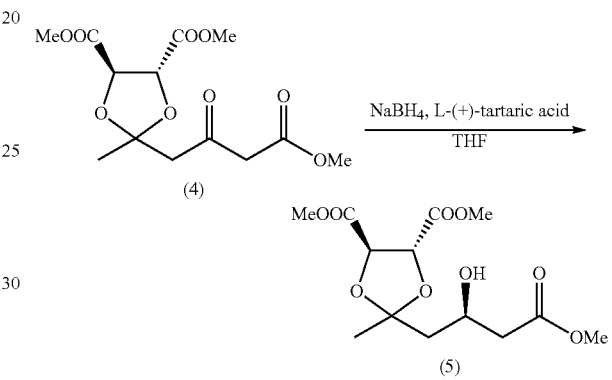

In a two necked round bottom flask (50 ml) under Ar, L-tartaric acid (315 mg, 2.09 mmol, 4 eq) was added to a suspension of NaBH$_4$ (79 mg, 2.09 mmol, 4 eq) in THF (10 ml). The mixture was refluxed for 4 h, allowed to cool down to room temperature then to −10° C. A pre-cooled solution (−10° C.) of compound (4) (170 mg, 0.52 mmol, 1 eq) in THF (2 ml) was dropwise added. The reaction was left at T≤−10° C. for 2 h, then water (25 ml) was added. The aqueous phase was extracted with DCM. The pooled organic phases were dried over MgSO$_4$, filtered and the solvent removed under vacuum. The obtained crude was purified through SiO$_2$ gel automatic column chromatography, eluting with 8:2 Cyclohexane/Ethyl acetate. The pooled fractions gave 97 mg (58%) of clean (5) having e.e. 94%.

Example 14

Screening of the Ketoreductase Enzyme for Synthesis of Methyl (3R)-3-hydroxy-4-(2-methyl-1,3-dioxolan-2-yl)butanoate (3).

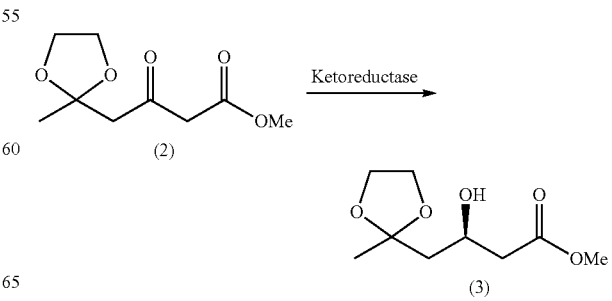

A enzymatic screening was performed on substrate (2) (prepared according to step b) of experiment 12) in a phosphatebuffer 250 mM, pH 7, with 2 mM magnesium phosphate, 1.1 mM NADP+, 1.1 NAD+, 80 mM Glucose, 10 U/ml Glucose dehydrogenase GDH-105 (Codexis). Reactions were performed in 2 ml reaction volume with 8 mg of substrate (2), 2 mg of enzyme (or 0.4 U for enzyme 17beta-HSD5 recombinant murine (SEQ. ID n.2) from WO2011/000693). The reactions, at different level of conversion, were analysed after 24 h for e.e. estimation of product (3) using a Chiralpack AD-RH 150 mm×4.6 mm×5 μm.

The following table summarized the results achieved.

TABLE 3

| Ketoreductase Enzyme (Source) | Conversion (%) | e.e. for R enantiomer % |
| --- | --- | --- |
| KRED-119 (Codexis) | 86.3 | 34.5 |
| KRED-130 (Codexis) | 100 | >99.9 |
| KRED-P1-A04 (Codexis) | 2.9 | >99.9 |
| KRED-P1-B02 (Codexis) | 5.7 | 32.7 |
| KRED-P1-C01 (Codexis) | 9.1 | 25.1 |
| KRED-P2-D11 (Codexis) | 4.5 | 22.6 |
| KRED-P1-H10 (Codexis) | 3 | >99.9 |
| Enzyme 17beta-HSD5 recombinant murine (SEQ. ID n. 2 from WO2011/000693) | 100 | >99.9 |

The enzyme KRED-130 (Codexis) and the enzyme 17beta-HSD5 recombinant murine (SEQ. ID n.2) from WO2011/000693 were further investigate for best condition setting. By monitoring NADPH consuming at 340 nm with spectrophotometer it were estimated the activity at different pH and substrate (2) concentrations for KRED 130 (Codexis) and ketoreducatase from WO2011/000693. The better pH for KRED-130 results between 6.5 and 8, being 7 the best value and Km was 30.7 mM, while for ketoreducase from US2011207172 better pH is between 5 and 6, with best results at pH 5.5 and Km 3.4 mM.

Example 15

Experiments with Ketoreductase KRED-130.

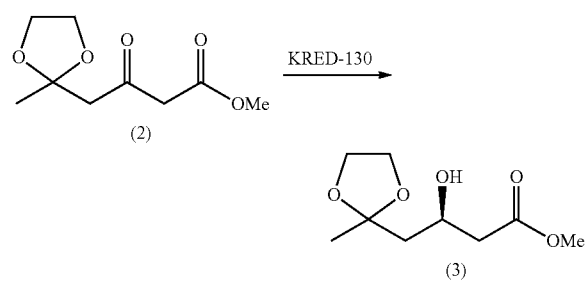

In a thermostated reactor at 20° C., 0.5 g of substrate (2) was completely convert to product (3) in 53 h in 30 ml of phosphate buffer 100 mM pH 7.5 with 0.9 g of glucose, 25 mg of NADP+ sodium salt, 5 mg of glucose dehydrogenase CDX-901 (Codexis), using 10 mg of ketoreductase KRED-130 (Codexis). The reaction was performed using automatic pH stat that maintain the pH of 7.5 with addition of 0.5 M NaOH. Once reaction was complete the reaction was filtered on dicalite and extract with 60 ml of MTBE. The extract was filtered on paper and bought to residue giving 0.50 g of isolated product (3) with an e.e. >99.9% (the other isomer is not detected).

Similarly in a thermostated reactor at 30° C., 1 g of substrate (2) was converted at 92.7% in 21 h to product (3). The reaction was performed in 25 ml of phosphate buffer 100 mM pH 7 with 1.8 g of glucose, 13 mg of NADP+ sodium salt, 5 mg of glucose dehydrogenase CDX-901 Codexis, 6 mg of magnesium sulphate and using 20 mg of ketoreductase KRED-130. The reaction was performed using automatic pH stat that maintain the pH of 7 with addition of 0.5 M NaOH. After said hours the reaction was saturated with NaCl, filtered on dicalite and extract with 150 ml of toluene. The organic phase was filtered on paper and bought to residue giving 0.365 g of isolated product (3).

Similarly in a thermostated reactor at 30° C., 10 g of substrate (2) (with 90% purity (GC A %)) was converted at 98.4% in 42 h to product (3). The reaction was performed in 200 ml of phosphate buffer 100 mM pH 7 with 15 g of glucose, 100 mg of NADP+ sodium salt, 50 mg of glucose dehydrogenase CDX-901 Codexis, 50 mg of magnesium sulphate and using 100 mg of ketoreductase KRED-130. The reaction was performed using automatic pH stat that maintain the pH of 7 with addition of 2 M NaOH. After said hours the reaction was filtered on dicalite, saturated with NaCl and extract with 420 ml of MTBE. The organic phases was dried with magnesium sulphate, filtered on paper and bought to residue giving 8.2 g of isolated product (3) (molar yield 90.4%) with a purity of 99.3% (GC A %). The product was analysed by NMR to confirm structure.

Similarly in a thermostated reactor at 30° C., 8 g of substrate (2) (with 89.2% purity (GC A %)) was converted at 99.6% in 42 h to product (3). The reaction was performed in 80 ml of phosphate buffer 50 mM pH 7 with 11 g of glucose, 40 mg of NADP+ sodium salt, 10 mg of glucose dehydrogenase CDX-901 Codexis, 20 mg of magnesium sulphate and using 80 mg of ketoreductase KRED-130. The reaction was performed using automatic pH stat that maintain the pH of 7 with addition of 2 M NaOH. After said hours the reaction was saturated with NaCl, filtered on dicalite and extract with 150 ml of EtAc. The organic phases was dried with magnesium sulphate, filtered on paper and bought to residue giving 6.5 g of isolated product (3) (isolated molar yield 90%), with a purity of 98.8% (GC A %).

Similarly in a thermostated reactor at 30° C., 7.15 g of substrate (89.6%, GC A %) was converted at 99.9% in 30 h to product. The reaction was performed in 20 ml of phosphate buffer 50 mM pH 7 with 11 g of glucose, 20 mg of NADP+ sodium salt, 10 mg of glucose dehydrogenase CDX-901 Codexis, 10 mg of magnesium sulphate and using 50 mg of ketoreductase KRED 130. The reaction was performed using automatic pH stat that maintain the pH of 7 with addition of 2 M NaOH. After said hours the reaction was saturated with NaCl, filtered on dicalite and extract with 120 ml of EtAc:IPA (9:1). The organic phases was dried with magnesium sulphate, filtered on paper and bought to residue giving 5.5 g of isolated product (purity 100% GC A %), isolated molar yield 85.8%).

Example 16

Experiments with Ketoreductase of WO2011/000693.

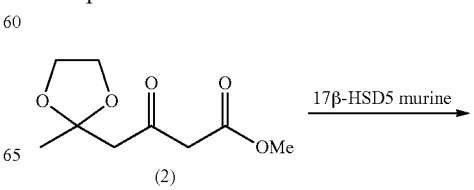

-continued

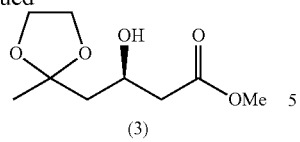

Note: the unities U are referred to Androstendione as substrate.

In a thermostated reactor at 25° C., 0.3 g of substrate (2) was partially converted to product (3) in 27 ml of phosphatebuffer 250 mM, pH 7, with 2 mM magnesium phosphate, 1.1 mM NADP+, 1.1 NAD+, 80 mM Glucose, 10 U/ml Glucose dehydrogenase GDH-105 (Codexis) and 10 U of enzyme 17beta-HSD5 recombinant murine (SEQ. ID n.2) of WO2011/000693. The reaction was performed using automatic pH stat that maintain the pH of 7 with addition of 0.5 M NaOH. After 20 h the reaction reach 18% of conversion with a e.e. >99.9%.

Similarly in a thermostated reactor at 20° C., 0.5 g of substrate (2) was partially converted to product (3). The reaction was performed in 25 ml of phosphate buffer 100 mM pH 5.5 with 0.9 g of glucose, 25 mg of NADP+ sodium salt, 5 mg of glucose dehydrogenase CDX-901 Codexis and using 5.8 U of ketoreductase enzyme 17beta-HSD5 recombinant murine (SEQ. ID n.2) of WO2011/000693. The reaction was performed using automatic pH stat that maintain the pH of 5.5 with addition of 0.5 M NaOH. After 19.5 h of reaction 25 mg of NADP+ sodium salt was added to reaction. At 41 h the reaction reach 12% of conversion with a e.e. >99.9%.

Similarly, in a thermostated reactor at 30° C., 6.7 g of substrate (purity 88.5% (GC A %)) was partially converted to product in 25 ml of phosphate buffer 50 mM pH 5.5 with 12.6 g of glucose, 25 mg of NADP+ sodium salt, 10 mg of glucose deydrogenase CDX-901 Codexis and using 66 U of ketoreductase (SEQ. ID n.2) of WO2011/000693. The reaction was performedusing automatic pH stat that maintain the pH of 5.5 with addition of 1 M NaOH and adding 25 mg NADP+ sodium salt every 8 h. At 55 h the reaction was saturated with NaCl, filtered on dicalite and extract with 150 ml of MTBE. Organic phase was dehydrated with magnesium sulphate and filtered on paper. At residue it was obtained 3.9 g of product (3) (purity 82% (GC A %), molar yield 56%).

Similarly, in a thermostated reactor at 30° C., 2 g of substrate (GC) was converted to product in 25 ml of phosphate buffer 50 mM pH 5.5 with 3.6 g of glucose, 25 mg of NADP+ sodium salt, 10 mg of glucose deydrogenase CDX-901 Codexis and using 58 U of ketoreductase (SEQ. ID n.2) of WO2011/000693. The reaction was performed using automatic pH stat that maintain the pH of 5.5 with addition of 1 M NaOH and adding 25 mg NADP+ sodium salt every 8 h. At complete conversion (30 h) the reaction was saturated with NaCl, filtered on dicalite and extract with 80 ml of EtAc. Organic phase was dehydrated with magnesium sulphate and filtered on paper. At residue it was obtained 1.5 g of product (3) (purity 79% (GC A %), molar yield 66%).

Experiment 17

Synthesis of Methyl (3R)-3-hydroxy-5-oxohexanoate (6)

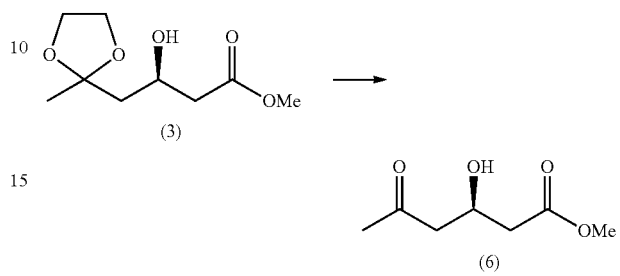

To a solution of Methyl (3R)-3-hydroxy-4-(2-methyl-1,3-dioxolan-2-yl)butanoate (3) (5 g, 24.5 mmol) (as prepared in Experiment 15) in a mixture of acetone/water (2:1, 30 mL), pyridiniumtosylate (1.84 g, 7.34 mmol) was added and the reaction mixture was refluxed (60° C.) for 1-2 hours. After removing the solvent under vacuum, a 10% NaHCO$_3$ solution was added and extracted with dichloromethane (3×30 mL). The combined organic phases was evaporated under reduced pressure to give methyl (3R)-3-hydroxy-5-oxohexanoate (6) as an oil (3.33 g, 85%).

Experiment 18

Synthesis of compound of formula (II-R, PG=TDBMS, Z=OMe)

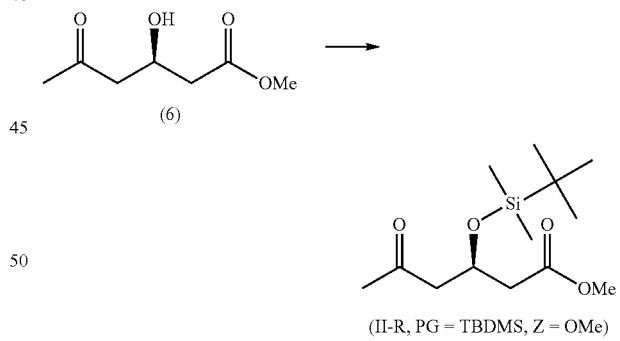

Methyl (3R)-3-hydroxy-5-oxohexanoate (6) (10 g, 0.062 mol) was dissolved in dry DMF (110 mL) and the solution was cooled down to 0° C. Imidazole (8.5 g, 0.124 mol) and tert-butyldimethylsilyl chloride (11.3 g, 0.0744 mol) were added. The reaction mixture was stirred at 25° C. for 12 h and then quenched with a 10% NaHCO$_3$ solution. After the extraction with toluene (3×150 mL), the collected organic phase was dried under vacuum and the resulted oil was purified via by fractional distillation. Methyl (3R)-3-(tert-butyldimethylsiloxy)-5-oxohexanoate was obtained as a yellow oil the compound of formula (II-R, PG=TDBMS, Z=OMe)(11.3 g; molar yield 66%).

Experiment 19

Synthesis of Methyl (3R)-3-(tert-butyldimethylsiloxy)-4-(2-methyl-1,3-dioxolan-2-yl)butanoate (7)

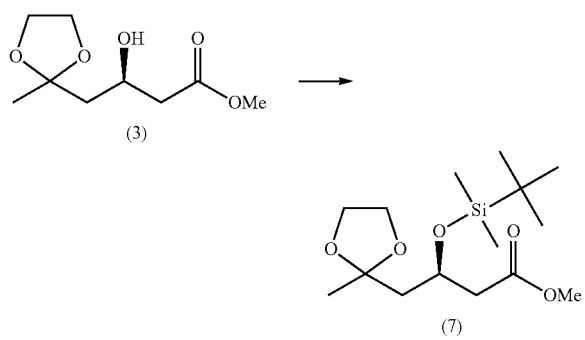

Methyl (3R)-3-hydroxy-5-oxohexanoate (6 g, 0.029 mol) was dissolved in dry DCM (70 mL) and the solution was cooled down to 0° C. Imidazole (3.8 g, 0.056 mol) and tert-butyldimethylsilyl chloride (5.1 g, 0.035 mol) were added. The reaction mixture was stirred at room temperature (25° C.) for 12 h and then quenched with a 10% NaHCO$_3$ solution. After the extraction with toluene (3×70 mL), the collected organic phase was concentrated under vacuum and the resulted oil was purified by fractional distillation (9.2 g of compound of formula (7), 98% molar yield). H-NMR of compound (7):

$^1$H-NMR (400, MHz) δ: 4.31 (m, 1H), 3.94-3.90 (m, 4H), 3.65 (s, 3H), 2.77 (dd, J=14.8, 4.0 Hz, 1H), 2.42 (dd, J=15.2, 8 Hz, 1H), 1.92 (d, J=5.6 Hz, 2H), 1.91 (s, 1H), 1.34 (s, 3H), 0.84 (s, 9H), 0.07 (s, 3H), 0.04 (s, 3H).

Experiment 20

Synthesis of compound of formula (II-R, PG=TDBMS, Z=OMe)

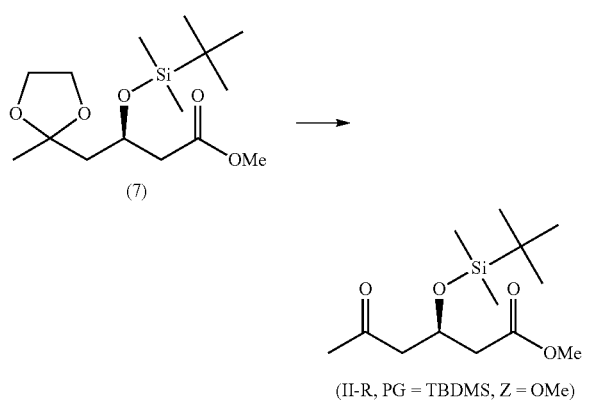

To a solution of Methyl (3R)-3-(tert-butyldimethylsiloxy)-4-(2-methyl-1,3-dioxolan-2-yl)butanoate (7) (300 mg, 0.94 mmol) in acetone (4 mL), pyridiniumtosylate (71 mg, 0.28 mmol) was added and the reaction mixture heated at 40° C. for 2 days. After removing the solvent under vacuum, a 10% NaHCO$_3$ solution was added and extracted with dichloromethane (3×10 mL). The combined organic layers were evaporated under reduced pressure to give the oily methyl-(3R)-(tert-butyldimethylsiloxy)-5-oxohexanoate (225 mg, 87%).

Experiment 21

Synthesis of compound of formula (II-R, PG=TBDMS, Z=OMe)

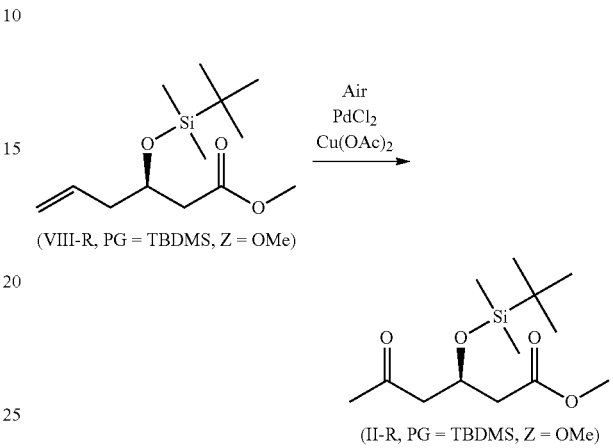

A stirred solution of PdCl$_2$ (14 mg, 0.08 mmol, 0.1 eq) and Cu(OAc)$_2$ (28 mg, 0.15 mmol, 0.2 eq) in a mixture of DMF/H2O 7:1 (4.0 mL) was bubbled with air in the dark for 30 min. Compound (VIII-R, PG=TBDMS, Z=OMe) (200 mg, 0.77 mmol, 1.0 eq) was added dropwise and the mixture stirred at room temperature. After 2 days, the reaction mixture was added to H$_2$O (20 mL) and extracted with EtOAc (3×15 mL). The combined organic extracts were washed with water (2×10 mL), dried over MgSO$_4$, filtered and the solvent removed under vacuum. Compound (II-R, PG=TBDMS, Z=OMe) was isolated together with Aldehyde side product as a 85:15 mixture (248 mg, 99% yield).

$^1$H-NMR (400 MHz, CDCl$_3$) δ=0.03 (s, 3H, Si—CH3), 0.05 (s, 3H, Si—CH$_3$), 0.82 (s, 9H, 3×CH$_3$, Si-tBu), 2.14 (s, 3H, COCH$_3$), 2.49 (m, 2H, CH$_2$CO), 2.68 (m, 2H, CH$_2$CO), 3.64 (s, 3H, COOCH$_3$), 4.54 (m, 1H, CHOTBS).

$^{13}$C-NMR (75 MHz, CDCl$_3$) δ=−5.0 (CH$_3$, Si—CH$_3$), −4.9 (CH$_3$, Si—CH$_3$), 17.8 (Cq, Si-tBu), 25.6 (3×CH$_3$, Si-tBu), 31.3 (CH$_3$, CH$_3$CO), 42.2 (CH$_2$, CH$_2$COOMe), 50.7 (CH$_2$, CH$_2$COMe), 51.5 (CH$_3$, COOCH$_3$), 65.7 (CH, CHOTBS), 171.4 (Cq, COOCH$_3$), 206.8 (Cq, COCH$_3$).

NMR characterization of the Aldehyde side product of formula:

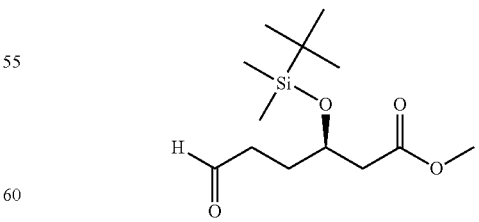

$^1$H NMR (400 MHz, CDCl$_3$) δ=0.04 (s, 3H, Si—CH$_3$), 0.06 (s, 3H, Si—CH$_3$), 0.85 (s, 9H, 3×CH$_3$, Si-tBu), 1.75-1.83 (m, 1H, CH$_2$), 1.85-1.94 (m, 1H, CH$_2$), 2.37-2.55 (m, 4H, 2×CH$_2$), 3.66 (s, 3H, COOCH$_3$), 4.2 (m, 1H, CHOTBS), 9.78 (s, 1H, CHO). $^{13}$C NMR (75 MHz, CDCl$_3$) δ=−5.0

($CH_3$, Si—$CH_3$), −4.7 ($CH_3$, Si—$CH_3$), 17.8 (Cq, Si-tBu), 25.6 (3×$CH_3$, Si-tBu), 29.3 ($CH_2$), 39.2 ($CH_2$), 42.4 ($CH_2$), 51.6 ($CH_3$, COO$CH_3$), 68.0 (CH, CHOTBS), 171.6 (Cq, COO$CH_3$), 201.8 (Cq, CHO).

Experiment 22

Synthesis of compound of formula (II-R, PG=TBDMS, Z=OMe)

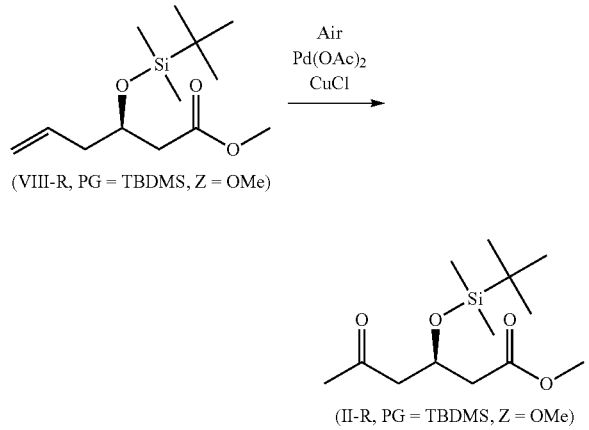 [SMILES: C=CC[C@H](CC(=O)OC)O[Si](C)(C)C(C)(C)C ; COC(=O)C[C@@H](CC(C)=O)O[Si](C)(C)C(C)(C)C]

A stirred solution of Pd(OAc)$_2$ (6 mg, 0.03 mmol, 0.1 eq) and CuCl (28 mg, 0.30 mmol, 1.0 eq) in a mixture of DMF/H2O 7:1 (1.5 mL) was bubbled with air in the dark for 30 min. Compound (VIII-R, PG=TBDMS, Z=OMe) (75 mg, 0.29 mmol, 1.0 eq) was added dropwise and the mixture was stirred at room temperature. After 16 h, the reaction mixture was added to H$_2$O (20 mL) and extracted with EtOAc (3×15 mL). The combined organic extracts were washed with water (2×10 mL), dried over MgSO$_4$, filtered and the solvent removed under vacuum. Compound (II-R, PG=TBDMS, Z=OMe) was isolated together with Aldehyde side product as a 85:15 mixture (82 mg, 87% yield).

Experiment 23

Treatment with NaHSO$_3$

In a 10 mL flask was prepared a suspension of NaHSO$_3$ (40 mg, 0.38 mmol, 0.3 eq) in H$_2$O (0.35 mL) and MeOH (0.35 mL). A solution of compound (II-R, PG=TBDMS, Z=OMe) (350 mg, 1.28 mmol, containing a ratio of product:aldehyde side product 80:20) in 2-MeTHF (1.75 mL) was added and the mixture was stirred at 40° C. for 2 h. The resulting suspension was filtered and the solid was washed with 2-MeTHF (0.35 mL, 1 vol). The filtrate was washed with H$_2$O (3×2 mL), was dried over MgSO$_4$ and was evaporated under reduced pressure to afford the compound (II-R, PG=TBDMS, Z=OMe)(151 mg, 43% yield, Ratio product/aldehyde side product=99:1).

Experiment 24

Synthesis of compound of formula (II-R, PG=TDBMS, Z=OMe)

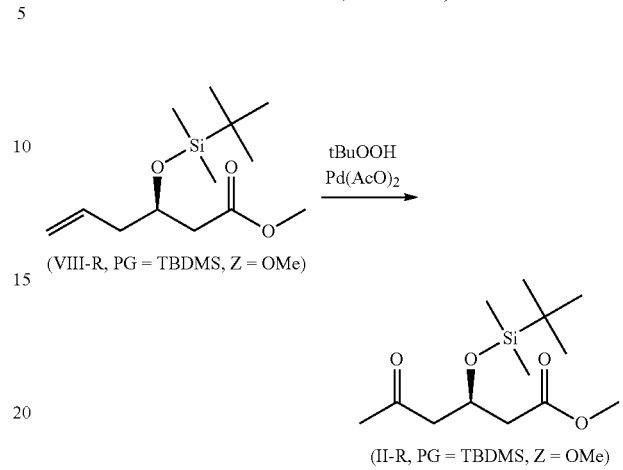

To a stirred mixture of Compound (VIII-R, PG=TBDMS, Z=OMe) (75 mg, 0.29 mmol, 1.0 eq) and Pd(OAc)$_2$ (3 mg, 0.01 mmol, 0.05 eq) in toluene, under nitrogen atmosphere, was added tBuOOH (0.29 mL, 3 M in isooctane, 0.87 mmol, 3.0 eq). The mixture was stirred for 16 h at room temperature. Extra Pd(OAc)$_2$ (5 mg, 0.02 mmol, 0.10 eq) was added, the mixture was heated to 55° C. and stirring was continued for 16 h. The mixture was diluted with EtOAc (10 mL) and cooled to 0° C. with stirring. Saturated aqueous Na2S2O3 (20 mL) was added and the organic layer was separated. After washing with additional saturated aqueous Na$_2$S$_2$O$_3$ and saturated aqueous NaCl, the organic phase was dried over MgSO$_4$, filtered and the solvent removed under vacuum to afford formula (II-R, PG=TDBMS, Z=OMe) (117 mg, quant. yield).

Experiment 25

Synthesis of compound of formula (II-R, PG=TDBMS, Z=OMe)

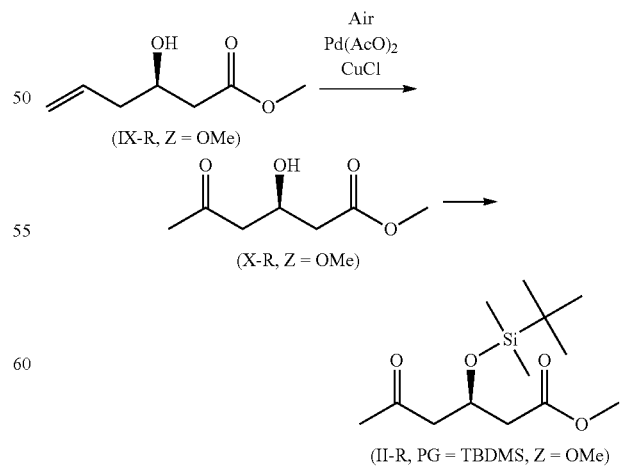

A stirred solution of Pd(OAc)$_2$ (12 mg, 0.05 mmol, 0.1 eq) and CuCl (51 mg, 0.52 mmol, 1.0 eq) in a mixture of DMF/H₂O 10:1 (2.2 mL) was bubbled with air in the dark for 30 min. Compound of formula (IX-R, Z=OMe) (75 mg, 0.52 mmol, 1.0 eq) was added dropwise and the mixture was stirred at room temperature for 16 h. The reaction mixture was added to H₂O (20 mL) and extracted with EtOAc (3×15 mL). The combined organic extracts were washed with water (2×10 mL), dried over MgSO₄, filtered and the solvent removed under vacuum. Treatment of the obtained crude with TBSCl (1.4 eq) and imidazole (2.3 eq) in CH₂Cl₂ for 2 h, provided formula (II-R, PG=TDBMS, Z=OMe) (89 mg, quant. yield, 50% purity), a pure sample of which was isolated after column chromatography.

The invention claimed is:

1. A compound of formula (II):

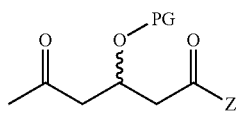

(II)

wherein the carbon substituted with —O-PG has an R configuration; and
wherein PG is a hydroxyl protecting group chosen from tetrahydropyranyl (THP), camphanoyl, bornyl, menthyl, R, (CO)R, CH₂OR, CH₂SR, and SiR₃, wherein R in SiR₃ is the same or different; and
wherein Z is chosen from OH, O⁻, OR, SR, O(CO)OR, NH₂, NHR, and NR₂;
wherein R in PG and Z is the same or different, and is chosen from linear or branched $C_{1-7}$ alkyl, linear or branched $C_{2-7}$ alkenyl, linear or branched $C_{2-7}$ alkynyl, $C_{3-7}$ cycloalkyl, and aryl-$C_{0-4}$ alkyl, and wherein in NR₂ the two R groups are optionally joined, forming a $C_{2-10}$ alkyl or alkenyl ring;
excluding compounds wherein:
Z is OEt and PG is TBDMS;
Z is OMe and PG is 4-Bromobenzoyl;
and
Z is OMe and PG is (S)-camphanoyl.

2. The compound according to claim 1, having the following formula (II-R):

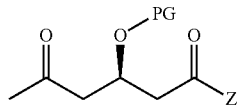

(II-R)

wherein Z is OtBu.

3. The compound according to claim 1, wherein PG is TBDMS, excluding compounds wherein Z is OEt.

4. The compound according to claim 3, having the following structure:

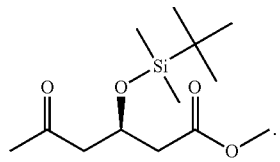 [SMILES: COC(=O)C[C@@H](CC(C)=O)O[Si](C)(C)C(C)(C)C]

* * * * *